United States Patent
Shiotsuka et al.

(10) Patent No.: US 7,700,374 B2
(45) Date of Patent: Apr. 20, 2010

(54) DEVICE FOR CAPTURING TARGET SUBSTANCE

(75) Inventors: Hidenori Shiotsuka, Kawasaki (JP); Takeshi Imamura, Chigasaki (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 11/916,254

(22) PCT Filed: Jun. 27, 2006

(86) PCT No.: PCT/JP2006/313195
§ 371 (c)(1),
(2), (4) Date: Nov. 30, 2007

(87) PCT Pub. No.: WO2007/004600
PCT Pub. Date: Jan. 11, 2007

(65) Prior Publication Data
US 2008/0206784 A1    Aug. 28, 2008

(30) Foreign Application Priority Data
Jun. 30, 2005  (JP) ............................ 2005-192084

(51) Int. Cl.
*G01N 33/553* (2006.01)
(52) U.S. Cl. ............... 436/525; 436/518; 436/524; 435/7.1; 435/283.1; 435/287.1; 435/288.7
(58) Field of Classification Search ............... 436/518, 436/524, 525; 435/7.1, 283.1, 287.1, 288.7
See application file for complete search history.

(56) References Cited

U.S. PATENT DOCUMENTS

| | | | |
|---|---|---|---|
| 5,492,840 A * | 2/1996 | Malmqvist et al. | .......... 436/518 |
| 5,665,597 A | 9/1997 | Imamura et al. | |
| 5,679,568 A | 10/1997 | Imamura et al. | |
| 5,693,527 A | 12/1997 | Imamura | |
| 5,803,664 A | 9/1998 | Kawabata et al. | |
| 5,807,736 A | 9/1998 | Kozaki et al. | |
| 5,854,059 A | 12/1998 | Kozaki et al. | |
| 5,863,789 A | 1/1999 | Komatsu et al. | |
| 5,945,331 A | 8/1999 | Kozaki et al. | |
| 5,962,305 A | 10/1999 | Mihara et al. | |
| 5,969,108 A | 10/1999 | McCafferty et al. | |
| 5,993,658 A | 11/1999 | Kato et al. | |

(Continued)

FOREIGN PATENT DOCUMENTS

| | | |
|---|---|---|
| WO | 88/06630 A1 | 9/1988 |
| WO | 92/15677 A1 | 9/1992 |
| WO | 92/15679 A1 | 9/1992 |

OTHER PUBLICATIONS

Limor Chen, et al., "Design and Validation of a Bifunctional Ligand Display System for Receptor Targeting", Chemistry & Biology, vol. 11, Aug. 2004, pp. 1081-1091.

James Light, et al., "Phophabs: Antibody-Phage-Alkaline Phosphatase Conjugates for One Step Elisa's Without Immunization", Bioorganic & Medicinal Chemistry Letters, vol. 2., No. 9, 1992, pp. 1073-1078.

Youngeun Kwon, et al., "Antibody Arrays Prepared by Cutinase-Mediated Immobilization on Self-Assembled Monolayers" Analytical Chemistry, vol. 76, No. 19, Oct. 1, 2004, pp. 5713-5720.

George P. Smith, "Filamentous Fusion Phage: Novel Expression Vectors that Display Cloned Antigens on the Virion Surface" Science, New Series, vol. 228, No. 4705, Jun. 14, 1985, pp. 1315-1317.

(Continued)

*Primary Examiner*—Melanie J. Yu
(74) *Attorney, Agent, or Firm*—Fitzpatrick, Cella, Harper & Scinto

(57) ABSTRACT

It is intended to provide a target substance-capturing body comprising: a base consisting of a soluble protein; and two or more functional domains capable of binding to different target substances.

5 Claims, 1 Drawing Sheet

U.S. PATENT DOCUMENTS

| | | |
|---|---|---|
| 6,004,772 A | 12/1999 | Imamura et al. |
| 6,017,746 A | 1/2000 | Imamura et al. |
| 6,096,530 A | 8/2000 | Kato et al. |
| 6,319,706 B1 | 11/2001 | Kawaguchi et al. |
| 6,472,191 B1 | 10/2002 | Yano et al. |
| 6,479,621 B2 | 11/2002 | Honma et al. |
| 6,586,562 B2 | 7/2003 | Honma et al. |
| 6,649,381 B1 | 11/2003 | Honma et al. |
| 6,660,516 B1 | 12/2003 | Imamura et al. |
| 6,686,439 B2 | 2/2004 | Kenmoku et al. |
| 6,803,444 B2 | 10/2004 | Suzuki et al. |
| 6,808,854 B2 | 10/2004 | Imamura et al. |
| 6,828,074 B2 | 12/2004 | Yano et al. |
| 6,855,472 B2 | 2/2005 | Imamura et al. |
| 6,858,367 B2 | 2/2005 | Yano et al. |
| 6,858,417 B2 | 2/2005 | Yano et al. |
| 6,861,496 B2 | 3/2005 | Kenmoku et al. |
| 6,861,550 B2 | 3/2005 | Honma et al. |
| 6,864,074 B2 | 3/2005 | Yano et al. |
| 6,867,023 B2 | 3/2005 | Honma et al. |
| 6,869,782 B2 | 3/2005 | Kenmoku et al. |
| 6,908,720 B2 | 6/2005 | Kenmoku et al. |
| 7,169,598 B2 | 1/2007 | Honma et al. |
| 7,354,995 B2 | 4/2008 | Imamura et al. |
| 2003/0044843 A1* | 3/2003 | Tanaka et al. ................ 435/7.1 |
| 2004/0105862 A1* | 6/2004 | Pan et al. ................ 424/146.1 |
| 2005/0221506 A1* | 10/2005 | Koo et al. ................... 436/525 |
| 2006/0115861 A1 | 6/2006 | Shiotsuka et al. |
| 2006/0275811 A1 | 12/2006 | Hatakeyama et al. |
| 2007/0298510 A1 | 12/2007 | Imamura et al. |
| 2008/0000308 A1 | 1/2008 | Kikuchi et al. |
| 2008/0108132 A1 | 5/2008 | Ban et al. |

OTHER PUBLICATIONS

Mitsuo Umetsu, et al., "How Additives Influence the Refolding of Immunoglobulin-folded Proteins in a Stepwise Dialysis System", Journal of Biological Chemistry, vol. 278, No. 11, Mar. 14, 2003, pp. 8979-8987.

Tomoichi Yokozeki, et al., "A Homogeneous Noncompetitive Immunoassay for the Detection of Small Haptens", Analytical Chemistry, vol. 74, No. 11, Jun. 1, 2002, pp. 2500-2504.

U.S. Appl. 11/995,911, International Filing Date: January 16, 2008: Applicants: Takeshi Imamura, et al.

U.S. Appl. No. 11/869,711, Filing Date: October 9, 2007: Applicants: Satoru Hatakeyama, et al.

Youngeun Kwon, et al., "Antibody Arrays Prepared by Cutinase-Mediated Immobilization on Self-Assembled Monolayers" Analytical Chemistry, vol. 76, No. 19, October 1, 2004, pp. 5713-5720.

George P. Smith, "Filamentous Fusion Phage: Novel Expression Vectors that Display Cloned Antigens on the Virion Surface" Science, New Series, vol. 228, No. 4705, June 14, 1985, pp. 1315-1317.

Mitsuo Umetsu, et al., "How Additives Influence the Refolding of Immunoglobulin-folded Proteins in a Stepwise Dialysis System", Journal of Biological Chemistry, vol. 278, No. 11, March 14, 2003, pp. 8979-8987.

Tomoichi Yokozeki, et al., "A Homogeneous Noncompetitive Immunoassay for the Detection of Small Haptens", Analytical Chemistry, vol. 74, No. 11, June 1, 2002, pp. 2500-2504.

* cited by examiner

DEVICE FOR CAPTURING TARGET SUBSTANCE

TECHNICAL FIELD

The present invention relates to a target substance-capturing body for capturing a target substance and to a method, a test kit, and so on, for detecting a target substance by use of the target substance-capturing body.

BACKGROUND ART

Biomolecules specifically binding to target substances or low molecular compounds whose target molecules are biomolecules have been expected to be used as candidate substances for pharmaceutical drugs which exert effective physiological activities in vivo on the basis of their specific binding functions to target substances or for target substance-capturing bodies of biosensors.

An example of the biopolymers as described above can include antibodies. The antibody is one of proteins that function in the self-defense mechanisms of animals through which various foreign substances invading their body fluids are detoxicated by the immune systems. In other words, the immune system recognizes a variety of structures on the surface of the foreign substance and produces antibodies specifically binding thereto. As a result, the specific binding of the antibody to the foreign substance detoxicates the foreign substance through the in-vivo immune system. To effectively exert this mechanism, antibodies possess molecular diversity (the number of antibodies with different amino acid sequences for binding to various foreign substances), and the number of antibodies per individual animal is estimated to be $10^7$ to $10^8$. Their specificity in antigen recognition, high antigen-binding ability and molecular diversity account for expectations placed on the use of the antibodies as candidate substances for pharmaceutical drugs or as target substance-capturing bodies.

An antibody has a structure formed by two long and two short polypeptide chains. The long polypeptide chains and the short polypeptide chains are called heavy chains and light chains, respectively. These heavy and light chains individually have variable and constant regions. The light chain is a polypeptide chain composed of two domains, one variable region (VL) and one constant region (CL). The heavy chain is a polypeptide chain composed of four domains, one variable region (VH) and three constant regions (CH1 to CH3).

Each domain of the antibody assumes a tubular structure consisting of approximately 110 amino acids and forms a very stable structure where layers are formed by β-sheets arranged in an antiparallel orientation and are further bound with each other through SS-bond.

The binding of the antibody to various antigen species is known to result from the diversity of amino acid sequences of three complementarity determining region (CDR) retained in each variable region (VH or VL). These three CDRs residing in each of VH and VL are partitioned by framework regions and allow for more highly specific molecular recognition by recognizing the spatial arrangement of a substance to be recognized. The diversity of CDR is generated by DNA reorganization occurring in the antibody gene loci when bone marrow stem cells are differentiated into B lymphocytes, antibody-producing cells. This diversity is known to be produced by causing the DNA reorganization in portions composed of VH, D and JH gene fragments in the heavy chain and in portions composed of Vλ or Vκ gene fragments or Jλ or Jκ gene fragments in the light chain. These genetic recombination processes allow for the molecular diversity of the antibody.

Such antibodies capable of binding to particular substances have conventionally been produced in artificial manners utilizing the antibody production mechanisms in the immune systems of animals as described above and have been used in various industrial fields. One example of the production method thereof includes a method involving immunizing animals (e.g., rabbits, goats and mice) to be immunized with antigen substances of interest together with adjuvants at certain intervals and collecting antibodies produced in their sera. The antibodies thus obtained are a mixture of plural antibodies that recognize various structures present on the surfaces of the antigen substances used in the immunization. The sera containing plural antibodies binding to single antigens as described above are called polyclonal antibodies.

On the other hand, the DNA reorganization occurs independently in each B cell. Therefore, one B cell produces only one type of antibody. To obtain single antibodies, a method involving fusing B cells producing particular antibodies with established tumor cells to produce hybridoma cells has been established. The single antibodies produced from such hybridomas are called monoclonal antibodies.

Antibody fragments Fab, Fab' and F(ab')2 obtained by treating the antibodies as described above with a certain kind of proteolytic enzyme are known to have binding ability to the same antigen as those against their parent antibodies and known to be sufficiently available as target substance-capturing bodies.

As described above, such antibodies or antibody fragments are widely available as target substance-capturing bodies adapted for target molecules in biosensors. In this case, the antibodies or antibody fragments are generally immobilized for use on a substrate. A method used for immobilizing the antibodies or antibody fragments are generally selected from physical adsorption and chemical crosslinking methods. In the immobilizing method using physical adsorption, a site of the protein involved in the adsorption cannot be selected arbitrarily when physically adsorbed onto the substrate. Alternatively, in the immobilizing method using chemical bond caused by crosslinking reaction, a functional group of the protein involved in reaction with a crosslinking agent cannot be determined arbitrarily in most cases. Furthermore, when there exist plural reactable functional groups, selectivity among them is exceedingly low. In binding to the substrate through physical adsorption or through chemical bond caused by crosslinking reaction, a site of the protein involved in the binding is generally selected at random. Therefore, if a site directly or indirectly involved in the target substance-binding ability of a protein is identical or overlaps with a site involved in binding onto substrate surface, the target substance-binding ability of the protein might be reduced remarkably.

Moreover, studies have been conducted, which apply Fab and Fab' fragments containing heavy chain variable regions (VH) and light chain variable regions (VL) that are antibody recognition domains or containing constant regions CH1 and CL for stabilizing them more highly, camel heavy-chain antibody variable regions (VHH), VH and VL. In these studies, a single chain antibody (scFv) is produced in a genetic engineering manner by fusing VH, VL, and so on via amino acids called linkers, and applied as a target substance-capturing body.

For a method for immobilizing such antibody fragments onto a substrate, their features of being able to be produced in a genetic engineering manner have been exploited to study a method involving fusing substrate-affinity peptides or biological compounds (e.g., enzymes) with affinity for compounds immobilized on the substrate into the antibody fragments in a genetic engineering manner. According to this method, such peptides or biological compounds can be selected and fused with the amino terminus (N terminus) or carboxy terminus (C terminus) of the produced antibody fragment molecules so as not to affect their desired antigen-binding ability. Therefore, the antibody fragments bound on the substrate can be expected to be oriented to some extent.

Examples of the substrate-affinity peptides include His tag composed of plural (usually five or more) consecutive histidine residues bonded together. If using a recombinant protein fused with this His-tag, it is possible to arrange desired target substance-capturing bodies on the substrate by applying coating capable of maintaining Ni ions to the substrate surface and utilizing the electrostatic binding between the Ni ions and the His tag.

Anal. Chem. 2004, 76, pp 5713-5720 has disclosed the use of a fusion protein comprising cutinase fused with the N terminus of scFv or the C terminus of VHH against hen egg lysozyme (HEL). This fusion protein is immobilized onto a substrate as follows: at first, SAM layers consisting of triethylene glycol sulfide displaying a suicide substrate for cutinase are formed on a gold substrate and thus the antibody protein of interest is immobilized onto the substrate via the irreversible binding between the suicide substrate and the cutinase. This document has also disclosed that the antibody fragment immobilized by this method exhibits desired binding ability.

A method for obtaining (producing) the antibodies or antibody fragments capable of being produced in a genetic engineering manner as described above is expected as follows: production methods or systems requiring low cost in total are expected to be adopted in consideration of investment in production facilities using prokaryotes typified by $E.\ coli$ as hosts, production control during the operation of the production facilities, etc. However, it is difficult to produce, in the prokaryotes, proteins derived from higher organisms including humans as active proteins that maintain desired functions. In many cases, general methods for this purpose have not been established.

A method selected for producing the antibody fragments typified by scFv and Fab in $E.\ coli$ is a method involving arranging a secretion signal such as pelB at the N terminus and allowing $E.\ coli$ to secrete the active antibody fragments into the periplasm or a culture supernatant by utilizing the mechanism of inner membrane transport. However, in such a method, antibody fragments cannot be obtained as secreted proteins for some types of antibodies of interest. For example, the desired antibody fragments are sometimes produced as an aggregate of insoluble fractions into the bacterial cell and are not secreted. In this case, the step of solubilizing the obtained aggregate with a denaturant such as guanidine hydrochloride and then refolding the protein structure into an active structure by a dilution or stepwise dialysis method is required and is operationally complicated. Moreover, active protein yields sometimes fall short of acceptable levels.

On the other hand, a method involving fusing the antibody fragments obtained in a genetic engineering manner with secretory proteins to efficiently obtain the antibody fragments as fusion proteins has been known. U.S. Pat. No. 5,969,108 has disclosed a technique for using the antibody fragment as described above as a phage antibody having a structure where the antibody fragment is fused with a coat protein of a phage, particularly a filamentous phage, and expressed and displayed on its surface.

In the production of phages displaying antibodies on their coat protein surfaces, a method involving selecting antibody fragment clones have been utilized as disclosed in the pamphlets of International Publication No. WO088/06630 and International Publication No. WO092/15677 in addition to U.S. Pat. No. 5,969,108 described above.

However, these documents have merely disclosed a method (antibody display method) for fusing an antibody of interest with a phage minor coat protein pIII (hereinafter, pIII) and has not specifically mentioned an antibody display method for other coat proteins. On the other hand, the pamphlet of WO092/15679 has disclosed a specific method for displaying a desired protein on a phage major coat protein pVIII (hereinafter, pVIII).

This document has gained the findings that an antibody protein displayed on pIII causes irreversible reaction with a target substance, and has released a technique for displaying a desired protein on pVIII and effects thereof.

However, all of the documents described above have merely disclosed the technique for displaying an antibody or desired protein on pIII and pVIII.

Descriptions suggesting the immobilization of these antibody fragment-fused phages on a particular substrate or the use of the immobilized phages rendered functional as sensing devices are not found in any of these documents.

On the other hand, Chemistry & Biology, Vol. 11, pp 1081-1091 has disclosed that labeled streptavidin can be detected on a cell.

More specifically, two different peptide chains are displayed on different coat proteins (pIII and pVIII) of a filamentous phage. The peptide chain (RGD-4C: CDCRGDCFC) displayed on the pIII is bound with a target substance (integrin) immobilized on a cell.

As a result, the phage is immobilized on the cell (KS1767) while the streptavidin-binding peptide (R5C2: ANRLCHPQFPCTSHE) is displayed on the pVIII of the phage. According to this document, the labeled streptavidin can thereby be detected on the cell. The document has also disclosed that the phage is bound with a substrate coated with streptavidin to detect the cell.

However, Chemistry & Biology, Vol. 11, pp 1081-1091 has demonstrated that difference in binding with the KS1767 cell is small between the RGD-4/R5C2 peptide-displaying phage and the R5C2-displaying phage. This indicates the low target substance-recognizing (binding) ability of the displayed RGD-4 peptide. Thus, this technique leaves room for improvements from the viewpoint of its use as a biosensing device that specifically detects a particular substance on a substrate.

The most important technique for producing and industrially using an excellent biosensing device is to produce binding molecules (e.g., antibodies) highly specific to target substances at high yields and immobilize the molecules on a substrate or the like with their activities maintained.

DISCLOSURE OF THE INVENTION

A target substance-capturing body of the present invention is characterized by comprising: a base consisting of a soluble protein; and two or more functional domains respectively capable of binding to different target substances.

An device for capturing a target substance of the present invention is an device for capturing a target substance characterized by having the constitution described above and comprising a substrate and the target substance-capturing body in which the two or more functional domains consist of a functional domain capable of binding to a substrate and a functional domain for capturing a target substance different from the substrate, wherein the substrate is bound with the functional domain adapted for the substrate, and the functional domain for capturing the target substance different from the substrate maintains its capturing function.

A detection instrument for detecting a target substance of the present invention is a detection instrument for detecting a target substance to be detected contained in an analyte characterized by comprising: the device of the constitution described above; and detection means for detecting the binding of a target substance to a functional domain for capturing a target substance to be detected comprised in the device.

A kit for detecting a target substance of the present invention is a kit for detecting a target substance to be detected contained in an analyte characterized by comprising: the device of the constitution described above; and detection means for detecting the binding of a target substance to a functional domain for capturing a target substance to be detected comprised in the device.

A method for detecting a target substance of the present invention is a method for detecting a target substance to be detected in an analyte characterized by comprising the steps of: reacting the device of the constitution described above with a target substance to be detected; and detecting the binding of the target substance to be detected to a functional domain of the device.

BEST MODE FOR CARRYING OUT THE INVENTION

Target Substance-Capturing Body

Figure 1:
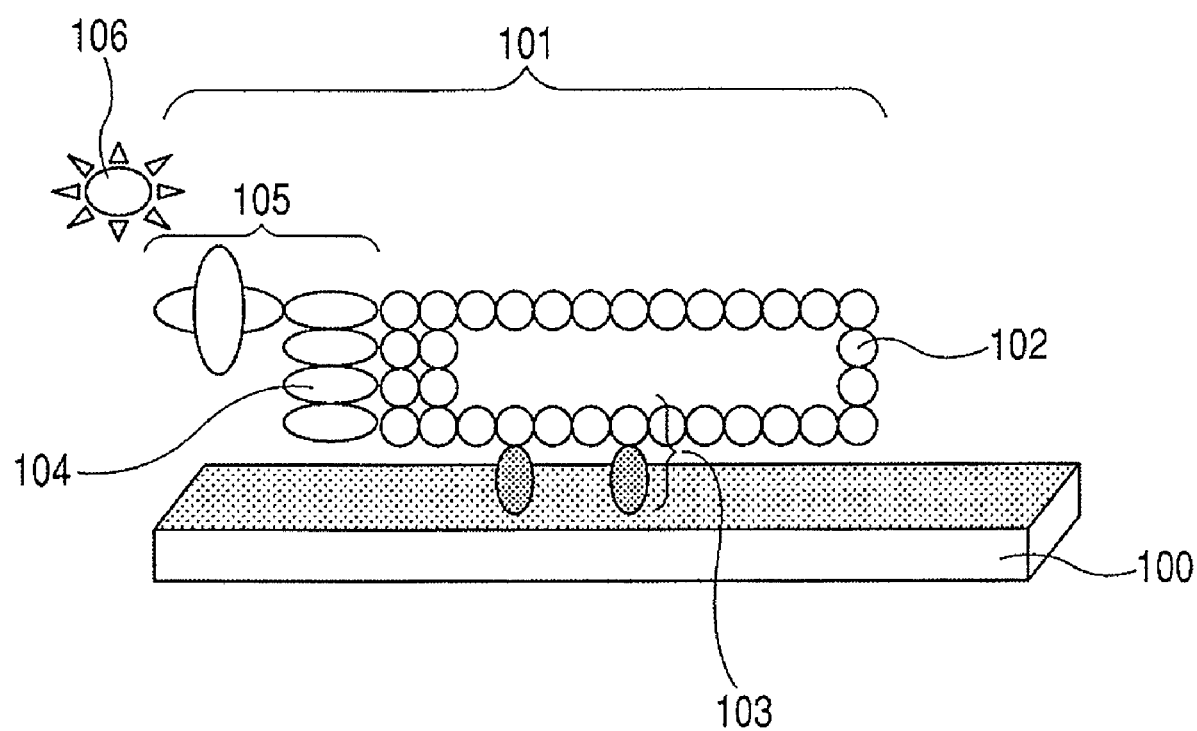
FIG. 1 is a diagram schematically showing the constitution of a target substance-capturing body according to the present invention.

A target substance-capturing body of the present invention is characterized by comprising a soluble protein and two or more functional domains binding to different target substances. In other words, the target substance-capturing body is a molecule having the functional domains binding to different target substances on the soluble protein used as a base (scaffold). Since the soluble protein is used as a scaffold, the target substance-capturing body has the feature of being easily suspended and solubilized in an aqueous solution. Furthermore, since the target substance-capturing body has the two or more functional domains binding to different target substances, one target substance-capturing body can capture two or more different target substances.

Here, the target substance-capturing body of the present invention will be described with reference to FIG. 1. FIG. 1 is a diagram schematically showing the constitution of the target substance-capturing body of the present invention. In FIG. 1, reference numeral 101 denotes one example of a target substance-capturing body (functional domain-displaying filamentous phage) of the present invention. Reference numerals 102 and 104 denote a pVIII protein and a pIII protein, respectively. These proteins correspond to the soluble proteins. Reference numerals 103 and 105 denote functional domain-fused VIII and functional domain-fused pIII, respectively. They have two functional domains binding to different target substances. Reference numerals 100 and 106 denote one example of a substrate used in the present invention and a target substance, respectively. The substrate 100 and the target substance 106 constitute the different target substances in this example.

Hereinafter, the target substance-capturing body of the present invention and materials preferable for the constitution of a device and so on by use of it will be described in detail.

(Soluble Protein)

The soluble protein used in the present invention functions as a base (scaffold) that holds the functional domains for capturing target substances as described above and also acts as a skeletal structure for obtaining the stable productivity of the target substance-capturing body. Any of previously known proteins may be used as the soluble protein. Particularly preferred is a protein stably present in an atmosphere (e.g., inside of cytoplasm or outside of cytoplasm containing periplasm fractions) in which the functional domains easily assume a structure for stably exerting their functions. Examples of the protein stably present inside of cytoplasm include glutathione-S-transferase and ribosome and β-galactosidase.

For example, the β-galactosidase is an enzyme consisting of a tetramer. Each subunit consists of three regions (N-terminal α-region, middle region and C-terminal ω-region). Even when these regions are separately expressed as their respective fragments, they are known to be spontaneously associated with each other. For example, an α-region-containing defective body/first capturing molecule and an ω-region-containing defective body/second capturing molecule are respectively produced and mixed together for these two molecules to be associated with each other as described above to function as one functional domain.

On the other hand, examples of the protein stably present in periplasm can include periplasm-localized disulfide bond-forming enzymes (DsbA), disulfide bond-isomerizing enzymes (DsbC) and peptidyl prolyl isomerase (PPI). Moreover, they may be fused with the functional domains. The functional domains may be displayed on (fused with) coat proteins of previously known phages, particularly filamentous phages, described below in detail.

The whole soluble protein having a given function may be used as the soluble protein used in the base of the target substance-capturing body of the present invention. Alternatively, not only the whole portion but also a portion of the protein can be used as long as it can maintain solubility and function as the base. When the soluble protein is a protein consisting of a complex of plural units as described above, the protein consisting of all the units may be used in the constitution of the base, or otherwise, each single unit selected therefrom may be used as the soluble protein.

Furthermore, the base may be composed of one soluble protein or plural soluble proteins.

(Filamentous Phage)

Phages capable of supplying the soluble protein to the target substance-capturing body include filamentous phages. Concrete examples thereof include f1, fd, M13, If1, Ike, Xf, Pf1 and Pf3. The fd and M13 phages whose life cycles as well as both genetic and virion structures are known in the art are particularly preferable because of being easily handled in a genetic engineering manner and relatively easily modified for desired properties. When the phage is used as a material for supplying the soluble protein, the phage is constructed as describe below.

It is preferred that the phage should have a structure in which two or more functional molecules of proteins for capturing target substances specifically binding to different target substances are displayed on one or more coat proteins selected from major and minor coat proteins composing the phage surface, that is, the phage shell.

Hereinafter, M13 will be described in detail as one example of the phage preferably used in the present invention with particular emphasis on parts related to the present invention.

(Major Coat Protein: pVIII)

The M13 major coat protein VIII (pVIII) is encoded by a portion called "gene VIII" (gVIII) and consists of 50 amino acids. The pVIII is synthesized as a pVIII precursor with 73 amino acids from the gVIII portion of an *E. coli*-infecting phagemid with the aid of protein synthetases of the host in the bacterial cell. The N-terminal 23 amino acids of the pVIII precursor are known to be a secretion signal peptide for transporting the synthesized pVIII precursor polypeptide into the cell membrane (inner membrane) After the cleavage of the signal sequence, the resulting pVIII is arranged in the form where its N terminus is embedded in the inner membrane.

(pVIII/Functional Domain Fusion Protein)

The following method is a method for displaying the desired functional domains including antibody fragments on the phage surface by fusing the functional domains with the pVIII so that they can sufficiently exert their functions: for example, a method involving constructing genes for expression on the basis of the technique disclosed in the pamphlet of WO92/15679 and a technique referring to it and expressing proteins onto the phage surface is preferably available. Specifically, a phagemid (recombinant gene) is constructed by functionally combining, if necessary, with a vector portion, (1) DNA encoding a signal sequence for guiding a protein of interest through the inner membrane to the surface;

(2) DNA encoding a desired functional domain; and (3) gVIII or DNA encoding N-terminally deleted pVIII so that desired expression is obtained. This phagemid is used to display a fusion protein between the pVIII and the functional domain on the phage surface or to obtain this fusion protein separated from the phage.

A protein having a previously known gene sequence and having a desired target substance-capturing function as the functional domain can be selected and used as the introduced functional domain. Among others, the preferable functional domain can include antibody fragments. The molecular size of the displayed functional domain is preferably approximately 250 amino acid residues, more preferably approximately 120 amino acid residues. The pVIII used for displaying the functional domain is a small protein with approximately 50 amino acid residues. Therefore, if the displayed functional domain is too large, it is difficult to display the functional domain together with the pVIII on the phage surface because the functional domain does not form the fusion protein with the pVIII and is taken up into the phage.

(Minor Coat Protein pIII)

The pIII is one of phage coat proteins encoded by gene III (gIII). A variety of documents and so on have demonstrated that the desired functional domain is expressed and displayed together with the pIII on the phage surface by inserting DNA encoding the functional domain of interest into the gIII.

(pIII/Functional Domain Fusion Protein)

A fusion protein between the pIII and the functional domain is supplied in the same way as in the pVIII described above by constructing phagemids encoding them and transforming *E. coli* hosts with the phagemids. However, the necessary infectivity of the phage for the host requires the binding of the N-terminal portion of the pIII with the F pili of the host *E. coli*. In this case, it is known that phage genome encoding a phage structural protein can be coinfected with a helper phage to thereby display the functional domain (ex. antibody fragment) on the pIII and produce the phage having infectivity. That is to say, it is possible to unevenly make five phage pIII proteins wild-type and fusion-type. In this context, a method for reducing replication efficiency by usually giving a slight defect to the IG (intergenic) region of the helper phage genome is known. When a phage carries phagemid encoding the gene of the antibody fragment to be displayed on pIII, it is known that a phage antibody with a pair of genotype of the phage and phenotype of the antibody fragment displayed on the phage. It is possible to select and produce DNA encoding the antibody fragment/pIII fusion protein in consideration of the function of the expressed antibody fragment with reference to documents such as Science, 1985, 228, 1315-1317.

(Functional Domain)

Two or more different functional domains for capturing target substances are used as the functional domains of the present invention. For example, a functional domain that captures a substrate as a target and a functional domain that captures a target substance to be detected are combined for use as the two or more different functional domains. As a result, a function as a biosensor immobilized on the substrate can be imparted to the target substance-capturing body. The functional domain functions for capturing a target substance, and the preferably used functional domain is capable of being expressed together with the soluble protein in a host and can be designed and produced by use of genetic engineering approaches. For example, the functional domain can be selected and used from proteins such as previously known enzymes and antibodies or functional peptide chains according to its use. Among them, the antibodies, particularly antibody fragments are desirable. The antibodies or antibody fragments have very stable structures, and it is possible to select therefrom those having strong target substance-binding ability. However, the whole antibody molecules are difficult to handle in a genetic engineering manner and still present many problems to be solved for current techniques, particularly in a simple production system using *E. coli*. In view of such productivity, the preferred embodiment of the present invention is an antibody fragment containing variable regions (VH and VL) or constant regions (CH1 and CL) that are target-binding regions of the antibody molecule or consisting of these regions. Moreover, the functional domain does not have to maintain the whole amino acid sequence or structure of this antibody fragment and may have the minimum amino acids and structure required to possess a desired function. Particularly when the functional domain is fused with pVIII, a low molecular functional domain is desirable as described above. The size of the functional domain used in the present invention is preferably 5 to 300 residues. The functional domain with 5 or more residues is known to have the binding ability to a particular substance. The functional domain with 300 or less residues can be expressed with its solubility maintained.

(Antibody Fragment)

The antibody fragment described in the present invention means a partial region of a monoclonal antibody.

Concrete examples thereof include Fab', Fab, Fd, Fv (variable fragment of antibody), scFv (single chain Fv) and dsFv (disulfide stabilised Fv). Alternative examples thereof include single domain antibodies (dAb) consisting of variable regions (VH) or light chain variable regions (VL). Furthermore, camel heavy-chain antibody variable regions (VHH), shark antibody-like molecules (IgNAR: immunoglobulin new antigen receptor), and so on may be applied thereto.

In this context, "F(ab')2" and "Fab'" are fragments that can be obtained by standard methods by treating antibodies with a proteolytic enzyme such as pepsin or papain. That is to say, they are antibody fragments produced as a result of digestion before and after disulfide bond located between two heavy chains (H chains) in the hinge region of the antibody.

The antibody fragment may also be an Fd fragment bound with VH and CH1. Furthermore, the antibody fragment may be an Fv (variable fragment of antibody) fragment or a portion thereof and may be, for example a heavy chain variable region (VH) or light chain variable region (VL) composing Fv or a portion thereof. On the other hand, single chain Fv (scFv) where the carboxy terminus of either of VH or VL is linked with the amino terminus of the other can also be used as a complex where VH and VL are arranged in a single-stranded polypeptide. It is desirable that a linker consisting of one or more amino acids should be provided between VH and VL (not in particular order) forming scFv. It is important to design the residue length of the amino acid linker so as not to provide binding force that prevents the formation of a structure necessary for the binding of VH or VL with an antigen. Specifically, the length of the amino acid linker is generally 5 to 18 residues, and the amino acid linker with 15 residues has been used and studied most frequently. It is possible to obtain these fragments by genetic engineering approaches.

Furthermore, either of VH or VL may be the single domain dAb. However, because most single domain structures are generally unstable, it is preferred that such an unstable single domain dAb should be stabilized by chemical modification such as PEG modification.

(Substrate-Binding Antibody Fragment)

A target of the functional domain, for example the antibody or antibody fragment, displayed on the phage surface may be a substrate that forms a solid phase. For example, our studies have revealed those comprising one or more of SEQ ID NOs: 1 to 57 as antibody fragments showing binding properties to a gold substrate. Concrete examples of VH having SEQ ID NOs: 1 to 57 are shown in SEQ ID NOs: 58 to 74, and concrete examples of VL are shown in SEQ ID NOs: 75 to 77. Amino acid sequences derived from these amino acid sequences with the deletion, substitution or addition of one or several amino acids can be used without problems in the present invention as long as they are sequences that can exert gold-binding properties. One example of the nucleotide sequence of a gold-binding protein is shown below in SEQ ID NOs: 78 to 96.

Furthermore, the gold-binding protein can be constructed as described below.

In other words, it is possible to genetically modify a portion of a site that does not influence binding ability so much in the combination of VH and VL forming gold-binding domains to introduce a cysteine residue into the desired site of the VH and VL so that SS bond can be formed at an interface between the VH and VL. It is also possible to easily form a VH/VL complex by providing two cysteines in the linker.

(Others: Minor Coat Protein)

The introduced binding domains or epitopes can also be displayed as a portion of chimeric minor coat proteins on the filamentous phages. These minor coat proteins are encoded by "genes III, VI, VII and IX", and each of them is present in approximately 5 copies per virion and is involved in morphogenesis and infection. By contrast, the major coat protein is present in 2500 or more copies per virion. The proteins from the "genes III, VI, VII and IX" are located at the end of the virion.

(Target Substance)

In the present invention, any molecule may be used as a target substance to be captured as long as it is a substance that is capable of serving as an antigen in each approach using antigen-antibody reaction.

The target substances of the present invention are broadly classified into nonbiological substances and biological substances. The nonbiological substances of great industrial value can include:

PCBs as environmental contaminants with varying numbers/positions of substitution of chlorine; dioxins with varying numbers/positions of substitution of chlorine; and endocrine disruptors named so-called environmental hormones (e.g., hexachlorobenzene, pentachlorophenol, 2,4,5-trichloroacetic acid, 2,4-dichlorophenoxyacetic acid, amitrole, atrazine, alachlor, hexachlorocyclohexane, ethylparathion, chlordane, oxychlordane, nonachlor, 1,2-dibromo-3-chloropropane, DDT, kelthane, aldrin, endrin, dieldrin, endosulfan (benzoepin), heptachlor, heptachlor epoxide, malathion, methomyl, methoxychlor, mirex, nitrofen, toxaphene, trifluralin, alkylphenol (5 to 9 carbon atoms), nonylphenol, octylnonylphenol, 4-octylphenol, bisphenol A, di-2-ethylhexyl phthalate, butylbenzyl phthalate, di-n-butyl phthalate, dicyclohexyl phthalate, diethyl phthalate, benzo(a) pyrene, 2,4-dichlorophenol, di-2-ethylhexyl adipate, benzophenone, 4-nitrotoluene, octachlorostyrene, aldicarb, benomyl, kepone (chlordecone), manzeb (mancozeb), maneb, metiram, metribuzin, cypermethrin, esfenvalerate, fenvalerate, permethrin, vinclozolin, zineb, ziram, dipentyl phthalate, dihexyl phthalate and dipropyl phthalate).

Examples of the biological substances include biological substances selected from nucleic acids, proteins, sugar chains, lipids and complexes thereof. To be more specific, the biological substances comprise biomolecules selected from nucleic acid, protein, sugar chains and lipids.

Concretely, the present invention can be applied to any substance as long as it contains a substance selected from DNA, RNA, aptamers, genes, chromosomes, cell membranes, viruses, antigens, antibodies, lectin, hapten, hormones, receptors, enzymes, peptides, sphingoglycolipid and sphingolipid. In addition, bacteria and cells themselves that produce the "biological substances" can be target substances as the "biological substances" intended by the present invention.

Concrete examples of the proteins include so-called disease markers. Examples thereof include: α1-fetoprotein (AFP), an acid glycoprotein produced in hepatic cells for a fetal period and present in fetal blood, which serves as a marker for hepatocellular carcinoma (primary liver cancer), hepatoblastoma, metastatic liver cancer and yolk sac tumor; PIVKA-II, abnormal prothrombin appearing during hepatic parenchymal injury, which is confirmed to specifically appear in hepatocellular carcinoma; BCA225, a glycoprotein that is an antigen immunohistochemically specific for breast cancer, which serves as a marker for advanced primary breast cancer and recurrent/metastatic breast cancer; basic fetoprotein (BFP), a basic fetal protein found in extracts from human fetal serum, intestine and brain tissue, which serves as a marker for ovarian cancer, testicular tumor, prostatic cancer, pancreatic carcinoma, biliary tract carcinoma, hepatocellular carcinoma, renal cancer, lung cancer, gastric cancer, bladder carcinoma and colon cancer; CA15-3, a carbohydrate antigen, which serves as a marker for advanced breast cancer, recurrent breast cancer, primary breast cancer and ovarian cancer; CA19-9, a carbohydrate antigen, which serves as a marker for pancreatic carcinoma, biliary tract carcinoma, gastric cancer, liver cancer, colon cancer and ovarian cancer; CA72-4, a carbohydrate antigen, which serves as a marker for ovarian cancer, breast cancer, colorectal cancer, gastric cancer and pancreatic carcinoma; CA125, a carbohydrate antigen, which serves as a marker for ovarian cancer (particularly, serous cystadenocarcinoma), adenocarcinoma of the uterine body, cancer of the Fallopian tube, adenocarcinoma of the uterine cervix, pancreatic carcinoma, lung cancer and colon cancer; CA130, a glycoprotein, which serves as a marker for epithelial ovarian cancer, cancer of the Fallopian tube, lung cancer, hepatocellular carcinoma and pancreatic carcinoma; CA602, a core protein antigen, which serves as a marker for ovarian cancer (particularly, serous cystadenocarcinoma), adenocarcinoma of the uterine body and adenocarcinoma of the uterine cervix; CA54/61 (CA546), a core carbohydrate-related antigen, which serves as a marker for ovarian cancer (particularly, mucinous cystadenocarcinoma), adenocarcinoma of the uterine cervix and adenocarcinoma of the uterine body; carcinoembryonic antigen (CEA), which has currently been used most widely for assistance in diagnosing cancer as a marker antigen associated with cancer such as colon cancer, gastric cancer, rectal cancer, biliary tract carcinoma, pancreatic carcinoma, lung cancer, breast cancer, uterine cancer and urinary system cancer; DUPAN-2, a carbohydrate antigen, which serves as a marker for pancreatic carcinoma, biliary tract carcinoma, hepatocellular carcinoma, gastric cancer, ovarian cancer and colon cancer; elastase 1, an exocrine pancreatic protease present in the pancreas and specifically hydrolyzing elastic fiber elastin (composing arterial walls, tendons, and the like) in connective tissue, which serves as a marker for pancreatic carcinoma, cystic carcinoma of the pancreas and biliary tract carcinoma; immunosuppressive acidic protein (IAP), a glycoprotein present at high concentrations in the ascites and serum of human patients with cancer, which serves as a marker for lung cancer, leukemia, cancer of the esophagus, pancreatic carcinoma, ovarian cancer, renal cancer, cholangioma, gastric cancer, bladder carcinoma, colon cancer, thyroid carcinoma and malignant lymphoma; NCC-ST-439, a carbohydrate antigen, which serves as a marker for pancreatic carcinoma, biliary tract carcinoma, breast cancer, colon cancer, hepatocellular carcinoma, adenocarcinoma of the lung and gastric cancer; γ-seminoprotein (γ-Sm), a glycoprotein, which serves as a marker for prostatic cancer; prostate-specific antigen (PSA), a glycoprotein extracted from human prostate tissue and present only in prostate tissue, which thus serves as a marker for prostatic cancer; prostatic acid phosphatase (PAP), an enzyme secreted from the prostate and hydrolyzing phosphoric ester at acidic pH, which is used as a tumor marker for prostatic cancer; neuron-specific enolase (NSE), a glycolytic enzyme specifically present in nervous tissue and neuroendocrine cells, which serves as a marker for lung cancer (particularly, small cell carcinoma of the lung), neuroblastoma, nervous system tumor, islet cell cancer, small cell carcinoma of the esophagus, gastric cancer, renal cancer and breast cancer; squamous cell carcinoma-related antigen (SCC antigen), a protein extracted and purified from the hepatic metastatic foci of squamous cell carcinoma of the uterine cervix, which serves as a marker for uterine cancer (cervical squamous cell carcinoma), lung cancer, cancer of the esophagus, head and neck cancer and skin cancer; sialyl Le$^x$-i antigen (SLX), a carbohydrate antigen, which serves as a marker for adenocarcinoma of the lung, cancer of the esophagus, gastric cancer, colon cancer, rectal cancer, pancreatic carcinoma, ovarian cancer and uterine cancer; SPan-1, a carbohydrate antigen, which serves as a marker for pancreatic carcinoma, biliary tract carcinoma, liver cancer, gastric cancer and colon cancer; tissue polypeptide antigen (TPA), a single-stranded polypeptide useful for the speculation, prediction of recurrence, and observation of therapeutic process of advanced cancer particularly in combination with other tumor markers, which serves as a marker for cancer of the esophagus, gastric cancer, colorectal cancer, breast cancer, hepatocellular carcinoma, biliary tract carcinoma, pancreatic carcinoma, lung cancer and uterine cancer; sialyl Tn antigen (STN), a core carbohydrate antigen, which serves as a marker for ovarian cancer, metastatic ovarian cancer, gastric cancer, colon cancer, biliary system cancer, pancreatic carcinoma and lung cancer; cytokeratin (CYFRA) as an effective tumor marker for the detection of non-small cell carcinoma of the lung, particularly squamous cell carcinoma of the lung; pepsinogen (PG), an inactive precursor of two pepsins (PG I and PG II) that are proteases secreted into gastric juice, which serves as a marker for gastric ulcer (particularly gastric ulcer located in the lower part), gastroduodenal ulcer (particularly, recurrent and intractable cases), Brunner's gland adenoma, Zollinger-Ellison syndrome and acute gastritis; C-reactive protein (CRP), an acute phase reactant changed in serum by tissue injury or infection, which shows high values during myocardial necrosis caused by acute myocardial infarction and the like; serum amyloid A protein (SAA), an acute phase reactant changed in serum by tissue injury or infection; myoglobin, a heme protein with a molecular weight of approximately 17500 present mainly in cardiac muscles and skeletal muscles, which serves as a marker for acute myocardial infraction, muscular dystrophy, polymyositis and dermatomyositis; creatine kinase (CK; three isozymes of CK-MM type derived from skeletal muscles, CK-BB type derived from brains and smooth muscles, and CK-MB type derived from cardiac muscles, mitochondrial isozyme and immunoglobulin-linked CK (macro CK)), an enzyme present mainly in the soluble fractions of skeletal muscles and cardiac muscles and migrating into blood by cell injury, which serves as a marker for acute myocardial infraction, hypothyroidism, progressive muscular dystrophy and polymyositis; troponin T, a protein with a molecular weight of 39000 forming a troponin complex with troponin I and troponin C on the thin filaments of striated muscles and participating in the regulation of muscular contraction, which serves as a marker for rhabdomyolysis, myocarditis, myocardial infarction and renal failure; ventricular myosin light chain I, a protein contained in the cells of both skeletal muscles and cardiac muscles, which serves as a marker for acute myocardial infraction, muscular dystrophy and renal failure because a rise in its measurement result means injury and necrosis in skeletal muscles and cardiac muscles; and chromogranin A, thioredoxin and 8-OhdG, which are attracting attention as stress markers in recent years.

(Substrate)

A substrate with any material or shape can be used as the substrate according to the present invention as long as it achieves the object of the present invention. Particularly preferred is a substrate containing gold in at least a portion of its surface.

The material of the substrate used in the present invention may be any material that is capable of forming the structure of the present invention. The material is, for example a material comprising any one or more substances or a complex thereof selected from metals, metal oxides, inorganic semiconductors, organic semiconductors, glasses, ceramics, natural polymers, synthetic polymers and plastics.

The shape of the substrate used in the present invention may be any shape that is capable of forming the structure of the present invention, and is a shape comprising any one or more shapes selected from platelike, particulate, porous, protruded, fibrous, tubular and reticular forms.

Organic polymer compounds can include organic polymer compounds produced by polymerizing polymerizable monomers selected from the group consisting of: styrene-based polymerizable monomers such as styrene, α-methylstyrene, β-methylstyrene, o-methylstyrene, m-methylstyrene, p-methylstyrene, 2,4-dimethylstyrene, p-n-butylstyrene, p-tert-butylstyrene, p-n-hexylstyrene, p-n-octylstyrene, p-n-nonylstyrene, p-n-decylstyrene, p-n-dodecylstyrene, p-methoxystyrene and p-phenylstyrene; acryl-based polymerizable monomers such as methyl acrylate, ethyl acrylate, n-propyl acrylate, iso-propyl acrylate, n-butyl acrylate, iso-butyl acrylate, tert-butyl acrylate, n-amyl acrylate, n-hexyl acrylate, 2-ethylhexyl acrylate, n-octyl acrylate, n-nonyl acrylate, cyclohexyl acrylate, benzyl acrylate, dimethyl phosphate ethyl acrylate, diethyl phosphate ethyl acrylate, dibutyl phosphate ethyl acrylate and 2-benzoyloxyethyl acrylate; methacryl-based polymerizable monomers such as methyl methacrylate, ethyl methacrylate, n-propyl methacrylate, iso-propyl methacrylate, n-butyl methacrylate, iso-butyl methacrylate, tert-butyl methacrylate, n-amyl methacrylate, n-hexyl methacrylate, 2-ethylhexyl methacrylate, n-octyl methacrylate, n-nonyl methacrylate, diethyl phosphate ethyl methacrylate and dibutyl phosphate ethyl methacrylate; and vinyl-based polymerizable monomers such as esters of methylene aliphatic monocarboxylic acids, vinyl esters (e.g., vinyl acetate, vinyl propionate, vinyl butyrate, vinyl benzoate and vinyl formate), vinyl ethers (e.g., vinylmethyl ether, vinylethyl ether and vinylisobutyl ether) and vinyl ketones (e.g., vinyl methyl ketone, vinyl hexyl ketone and vinyl isopropyl ketone).

Examples of inorganic solid matter that can be used include: clay minerals such as kaolinite, bentonite, talc and mica; metal oxides such as alumina, titanium dioxide, zinc oxide, magnetite, ferrite, Nb—Ta complex oxides, $WO_3$, $In_2O_3$, $MoO_3$, $V_2O_5$ and $SnO_2$; insoluble inorganic salts such as silica gel, hydroxyapatite and calcium phosphate gel; metals such as gold, silver, platinum and copper; semiconductor compounds such as GaAs, GaP, ZnS, CdS and CdSe; and glass and silicon; and complexes thereof.

The substrate include: films consisting of plastics such as polyethylene terephthalate (PET), diacetate, triacetate, cellophane, celluloid, polycarbonate, polyimide, polyvinyl chloride, polyvinylidene chloride, polyacrylate, polyethylene, polypropylene and polyester: and porous polymer membranes consisting of polyvinyl chloride, polyvinyl alcohol, acetylcellulose, polycarbonate, nylon, polypropylene, polyethylene, Teflon, and the like. Alternatively, the substrate can be made into a membrane or sheet form by use of a wooden plate, a glass plate, a silicon substrate, cloth (e.g., cotton, rayon, acryl, silk and polyester) or paper (e.g., high-quality paper, medium-quality paper, art paper, bond paper, recycled paper, baryta paper, cast-coated paper, corrugated cardboard and resin-coated paper). The materials for these membrane or sheet forms may have smooth or uneven surfaces.

Further examples of the substrate include: substrates such as silicon, silica, glass and quartz glass, micro flow passages or holes provided in these substrates by approaches such as photolithography, etching and sandblasting, or those obtained by coating their surfaces with a thin membrane of gold, silver or platinum; substrates such as PDMS (polydimethylsiloxane), PMMA (polymethylmethacrylate), PET (polyethylene terephthalate), PC (polycarbonate) and PS (polystyrene) and micro flow passages or holes provided in these substrates by molding techniques; carbon nanotubes, carbon nanohorn, fullerene, diamond, and aggregates thereof; nanowhisker consisting of alumina, carbon, fullerene, ZnO, or the like; mesoporous thin films, microparticles and monolith structures consisting of $SiO_2$, aluminosilicate, other metallosilicates, $TiO_2$, $SnO_2$, $Ta_2O_5$, or the like; microparticles such as gold, silver, copper and platinum; metal oxide particles such as magnetite, ferrite, hematite, gamma-hematite and maghemite; aluminum-silicon mixture membranes and silicon oxide nanostructures obtained by anodically oxidizing them; porous alumina thin membranes, alumina nanohole structures and silicone nanowires.

(Use of Device)

The combination of the functional domain adapted for the substrate that captures the substrate as a target substance and has a substrate-binding property and the functional domain for detection that captures a target substance to be detected contained in a sample (analyte) as a target substance can be used as the functional domains comprised in the target substance-capturing body of the constitution described above.

More specifically, this target substance-capturing body is bonded with the substrate via the functional domain adapted for the substrate to form a device for detection. This device can be used to detect a target substance to be detected (e.g., a variety of nonbiological substances and biological substances described above) by use of the functional domain for detection. Moreover, at least this device and detection means (e.g., optical or electrical measurement instruments and a variety of reagents) capable of detecting the binding of the functional domain for detection with the target substance to be detected can be used to construct a detection instrument or detection kit.

A detecting method can include a method comprising the following steps:

(1) binding the target substance-capturing body to at least a portion of the surface of the substrate via its functional domain adapted for the substrate;

(2) contacting the substrate with an analyte (sample);

(3) washing the substrate; and (4) detecting a target substance to be detected captured by the functional domain for detection in the target substance-capturing body.

The detection in the step (4) can be performed by a optical detection method (e.g., a method using luminol reaction described in Examples below) using a substance with a detectable label specifically binding to the target substance-capturing body or the target substance to be detected, optical measurement applying enhanced Raman or localized plasmon principles to the use of the substrate having the surface consisting of gold or containing a portion consisting of gold, or electrical measurement utilizing its electrical properties. The specific operation of each of the steps can be performed based on a standard method.

On the other hand, the device for capturing a target substance according to the present invention is preferably available for use in the binding of two kinds of target substances by use of its capturing function and in the immobilization of a target substance onto the substrate by use of the functional domain adapted for the substrate when the target substance-capturing body is immobilized for use on the substrate.

EXAMPLES

Hereinafter, Examples of the present invention will be illustrated.

Example 1

Construction of Plasmid for Expression of pIII Fused with HEL-Binding scFv and Confirmation of its Expression M13KE (manufactured by NEW ENGLAND BIOLABS.) is used for pIII fusion protein expression. HEL-binding scFv (SEQ ID NO: 97 or 98) is inserted into the multicloning site of the M13KE. This plasmid is inserted into Acc65I/EagI according to the technical bulletin of the company. The resulting plasmid for expression is designated as pM13-HpIII. *E. coli* is transformed with pM13-GIII by electroporation according to the technical bulletin to express a phage displaying pIII fused with HEL-binding scFv.

The HEL-binding scFv is obtained as a DNA fragment encoding HEL-binding scFv by PCR using, as a template, a plasmid incorporating therein a HEL-binding scFv-encoding gene shown in Journal of Biological chemistry, 2003, 278, pp 8979. The following primers are used in this PCR:

```
scFv-f
NNNNCCATGCCCGATATCGTCCTGACCCAG    (SEQ ID NO: 112)

scFv-r
AGCTACCGCGGAGACGGTGACGAGGGT.      (SEQ ID NO: 113)
```

The following phage ELISA method is used in the confirmation of the expression:

(1) 80 μL each of serially diluted solutions of VH-displaying phage is dispensed to an amino-modified titer plate immobilizing HEL (manufactured by Seikagaku Corp.) thereon and gently stirred with a shaker for 1 hour;

(2) After the removal of the phage solutions, 90 μL of PBST is dispensed to each well and stirred for 10 minutes, followed by washing and discarding of the supernatant. This procedure is repeated three times;

(3) 75 μl of a solution of HRP-conjugated anti-M13 antibody/PBST (1/5000) is dispensed to each well and gently stirred with a shaker for 1 hour;

(4) The supernatant is discarded. Next, 90 μL of PBST is dispensed to each well and stirred for 10 minutes, followed by washing, and discarding of the supernatant. This washing procedure is repeated three times;

(5) 35 μL each of detection reagents 1 and 2 (Amersham BIOSCIENCE) is dispensed to each well and reacted for 1 minute with gentle stirring; and (6) The luminescence intensity of luminol is measured.

The same experiment except that M13KO7 (manufactured by NEW ENGLAND BIOLABS.) is used instead of pM13-HpIII is conducted as a comparative experiment. The phage obtained from the pM13-GpIII is confirmed to display gold-binding VH.

Example 2

Construction of Vector for Expression of pVIII Fused with SBA-15-Affinity Peptide The multicloning site BamHI/SpeI of an f1-based phagemid M13 mp18 (manufactured by NEW ENGLAND BIOLABS.) is used for pVIII fusion protein expression to construct a gene (SEQ ID NO: 101) having sequences in the following order:

(1) promoter sequence, (2) Shine-Dalgarno (SD) sequence, (3) M13-gVIII signal sequence-encoding DNA sequence, (4) SBA-15-affinity peptide-encoding DNA sequence (SEQ ID NO: 99), (5) M13-gVIII, (6) several termination codons, and (7) transcription terminator.

In this Example, the promoter sequence used is a tac promoter. The obtained plasmid is designated as pM13-SpVIII.

*E. coli* is transformed with this plasmid by electroporation according to the technical bulletin of the company to express a phage displaying pVIII fused with SBA-15. The following phage ELISA method is used in the confirmation of the expression:

(A) A solution of 1 mg of SBA-15/PBST and 80 μL of a phage solution are successively added to a 1.5-mL Eppendorf tube and gently stirred with a shaker for 1 hour;

(B) After centrifugation (15000 rpm, 10 min) and the removal of the supernatant solution, 1000 mL of PBST is dispensed again and stirred for 10 minutes, followed by washing and discarding of the supernatant. This procedure is repeated three times;

(C) 500 μl of a solution of HRP-conjugated anti-M13 antibody/PBST (1/5000) is added and gently stirred with a shaker for 1 hour;

(D) After centrifugation (15000 rpm, 10 min), the supernatant is discarded. Next, 1000 μL of PBST is dispensed and stirred for 10 minutes, followed by washing and discarding of the supernatant. This procedure is repeated three times;

(E) 35 μL each of detection reagents 1 and 2 (Amersham BIOSCIENCE) is dispensed to each well and reacted for 1 minute with gentle stirring; and (F) The luminescence intensity of luminol is measured.

The same experiment except that M13KO7 (manufactured by NEW ENGLAND BIOLABS.) is used instead of pM13-SpVIII is conducted as a comparative experiment. The phage obtained from the pM13-SpVIII is confirmed to display gold-binding VH.

Example 3

Construction of Plasmid for Coexpression of pIII Fused with HEL-Binding scFv/pVIII Fused with SBA-15-Affinity Peptide The pM13-HpIII obtained in Example 1 and the pM13-SpVIII obtained in Example 2 are used to construct a plasmid for coexpression of gold-binding VH-fused pIII/SBA-15-fused pVIII. The pM13-HpIII and the pM13-SpVIII cleaved with restriction enzymes BspHI/BsmI (both manufactured by NEW ENGLAND BIOLABS.) according to the method of the technical bulletin recommended by the manufacturer. The resulting enzyme reaction solution is subjected to agarose gel electrophoresis. A fragment of around 4.5 kbp obtained from the pM13-HpIII cleavage reaction solution and a fragment of around 0.6 kbp obtained from the pM13-SpVIII reaction solution are collected and purified with a purification kit (manufactured by Promega: trade name Wizard SV Gel and PCR Clean-Up System). Next, the DNA fragments thus obtained are ligated with T4-Ligase (manufactured by Roche) for 2 hours according to the method recommended by the manufacturer. The obtained ligation solution is transformed in the same way as in Example 2 to express and collect a phage. The following method is used in the confirmation of the expression:

(1) A solution of 1 mg of SBA-15/PBST and 80 μL of a phage solution are successively added to a 1.5-mL Eppendorf tube and gently stirred with a shaker for 1 hour;

(2) After centrifugation (15000 rpm, 10 min) and the removal of the supernatant solution, 1000 μL of PBST is dispensed again and stirred for 10 minutes, followed by washing and discarding of the supernatant. This procedure is repeated three times;

(3) Next, 1000 μL of 1 μM HEL is added and gently stirred with a shaker for 1 hour;

(4) After centrifugation (15000 rpm, 10 min) and the removal of the supernatant solution, 1000 μL of PBST is dispensed again and stirred for 10 minutes, followed by washing and discarding of the supernatant. This procedure is repeated three times;

(5) 500 μl of a solution of HRP-conjugated anti-HEL antibody/PBST (1/5000) is added and gently stirred with a shaker for 1 hour;

(6) After centrifugation (15000 rpm, 10 min), the supernatant is discarded. Next, 1000 μL of PBST is dispensed and stirred for 10 minutes, followed by washing and discarding of the supernatant. This procedure is repeated three times;

(7) 35 μL each of detection reagents 1 and 2 (Amersham BIOSCIENCE) is dispensed to each well and reacted for 1 minute with gentle stirring; and (8) The luminescence intensity of luminol is measured.

The experiments using the phages obtained in Examples 1 and 2 are performed as comparative experiments. The phage obtained in Example 3 is confirmed to have the highest luminescence intensity of luminol.

Example 4

Construction of Vector for Expression of pVIII Fused with Gold-Binding VH

The multicloning site BamH1/SpeI of an f1-based phagemid M13 mp18 (manufactured by NEW ENGLAND BIOLABS.) is used for pVIII fusion protein expression to construct a gene (SEQ ID NO: 102) having sequences in the following order:

(1) promoter sequence, (2) Shine-Dalgarno (SD) sequence, (3) M13-gVIII signal sequence-encoding DNA sequence, (4) gold-binding VH-encoding DNA sequence (SEQ ID NO: 80), (5) M13-gVIII, (6) several termination codons, and (7) transcription terminator.

In this Example, the promoter sequence used is a tac promoter. The obtained plasmid is designated as pM13-GpVIII. The gold-binding property of a phage obtained in the same way as in Example 2 by using the pM13-GpVIII is confirmed by the following method:

(A) 80 μL each of serially diluted solutions of VH-displaying phage is dispensed to a gold-deposited titer plate and gently stirred with a shaker for 1 hour;

(B) After the removal of the phage solutions, 90 μL of PBST is dispensed to each well and stirred for 10 minutes, followed by washing and discarding of the supernatant. This procedure is repeated three times;

(C) 75 μl of a solution of HRP-conjugated anti-M13 antibody/PBST (1/5000) is dispensed to each well and gently stirred with a shaker for 1 hour;

(D) The supernatant is discarded. Next, 90 μL of PBST is dispensed to each well and stirred for 10 minutes, followed by washing and discarding of the supernatant. This washing procedure is repeated three times;

(E) 30 μL each of detection reagents 1 and 2 (Amasham BIOSCIENCE) is dispensed to each well and reacted for 1 minute with gentle stirring; and (F) The luminescence intensity of luminol is measured.

The same experiment except that M13KO7 (manufactured by NEW ENGLAND BIOLABS.) is used instead of pM13-GVIII is conducted as a comparative experiment. The phage obtained from the pM13-GVIII is confirmed to display gold-binding VH.

Example 5

Construction of Plasmid for Coexpression of pIII Fused with HEL-Binding scFv/pVIII Fused with Gold-Binding VH The pM13-GpIII obtained in Example 4 and the pM13-SpVIII obtained in Example 2 are used to construct a plasmid for coexpression of gold-binding VH-fused pIII/SBA-15-fused pVIII. The pM1'-GpIII and the pM13-SpVIII are cleaved with restriction enzymes BspHI/BsmI (both manufactured by NEW ENGLAND BIOLABS.) according to the method of the technical bulletin recommended by the manufacturer.

The resulting enzyme reaction solution is subjected to agarose gel electrophoresis. A kbp fragment of the pM13-GpIII cleavage reaction solution and a kbp fragment of the pM13-SpVIII reaction solution are cleaved and purified with a purification kit (manufactured by Promega: trade name Wizard SV Gel and PCR Clean-Up System). Next, the DNA fragments thus obtained are ligated with T4-Ligase (manufactured by Roche) for 2 hours according to the method recommended by the manufacturer. The obtained ligation solution is transformed in the same way as in Example 2 to express and collect a phage.

The following method is used in the confirmation of the expression:

(1) 80 μL each of serially diluted solutions of VH-displaying phage is dispensed to a gold-deposited titer plate and gently stirred with a shaker for 1 hour;

(2) After the removal of the phage solutions, 90 μL of PBST is dispensed to each well and stirred for 10 minutes, followed by washing and discarding of the supernatant. This procedure is repeated three times;

(3) Next, 1000 μL of 1 μM HEL is added and gently stirred with a shaker for 1 hour;

(4) After centrifugation (15000 rpm, 10 min) and the removal of the supernatant solution, 1000 μL of PBST is dispensed again and stirred for 10 minutes, followed by washing and discarding of the supernatant. This procedure is repeated three times;

(5) 500 μl of a solution of HRP-conjugated anti-HEL antibody/PBST (1/5000) is added and gently stirred with a shaker for 1 hour;

(6) After centrifugation (15000 rpm, 10 min), the supernatant is discarded. Next, 1000 μL of PBST is dispensed and stirred for 10 minutes, followed by washing and discarding of the supernatant. This procedure is repeated three times;

(7) 35 μL each of detection reagents 1 and 2 (Amersham BIOSCIENCE) is dispensed to each well and reacted for 1 minute with gentle stirring; and (8) The luminescence intensity of luminol is measured.

The experiments using the phages obtained in Examples 2 and 4 are performed as comparative experiments. The phage obtained in Example 3 is confirmed to have the highest luminescence intensity of luminol.

Example 6

Construction of DsbA-Fused Gold-Binding VH/HEL-Binding scFv Complex

A target-capturing molecule of the present invention is constructed by the following steps and evaluated:

(1) Construction of DNA encoding gold-binding VH/HEL-binding scFv (1-1) DNA encoding gold-binding VH (SEQ ID NO: 80), a (GGGGS)$_3$ linker sequence and HEL-binding scFv (SEQ ID NO: 97) is constructed.

(1-2) The DNA is used as a template to perform amplification by PCR using the following primers:

```
7s4-fw-Ncol:
                                    (SEQ ID NO: 103)
ACATGCCATGGCCCAGGTGCAGTTGGTGGAGTCTG;
and HEL-bk-Hind3:
                                    (SEQ ID NO: 104)
AATGGCAAGCTTGGCCGTGATGATCAGCTTGGTA.
```

(1-3) The resulting PCR product is cleaved with NcoI/HindIII and inserted into pET-39b (manufactured Novagen). The cleavage with the restriction enzymes (NcoI and HindIII: manufactured by NEB) and the ligation reaction (T4-Ligase: manufactured by Roche) are performed according to the protocols recommended by the manufacturers.

(1-4) 5 μL of the ligation solution thus obtained is added to 50 μL of JM109 competent cells (manufactured by Promega) to perform transformation by heat shock.

(1-5) The cells are then developed onto a plate supplemented with LB/kanamycin (final concentration: 50 μg/mL) and left undisturbed at 37° C. Plasmids where the gene of interest is introduced are screened from the obtained colonies.

(2) Expression of Protein of Interest (2-1) The plasmids obtained in the step (1) are transformed into BL21 competent cells (manufactured by Promega). This transformation is performed by heat shock in the same way as in the step (1). The cells are then developed onto a plate with LB/kanamycin (final concentration: 50 μg/mL) and left undisturbed overnight at 28° C.

(2-2) The colonies obtained on the plate are poked with a toothpick, then transferred to a solution of 3 mL of LB/kanamycin, and cultured overnight at 28° C.

(2-3) The whole amount of the obtained culture solution is added to 250 mL of 2×YT medium (16 g of triptone, 10 g of enzyme extract and 5 g/L sodium chloride)/kanamycin medium and further cultured for around 8 hours.

(2-4) IPTG is added thereto at a time point of OD600=0.8 to induce the expression of the protein of interest. The overnight culture thereof is performed at 22° C.

(3) Collection of Protein of Interest (3-1) The culture solution obtained in the step (2) is centrifuged at 6000 rpm for 30 minutes to collect a supernatant. The weight of the supernatant is measured, and the supernatant is stored at 4° C.

(3-2) 60 wt % ammonium sulfate with respect to the weight of the supernatant is added in four portions with stirring, and this stirring is continued for 6 hours.

(3-3) The obtained suspension is centrifuged at 8000 rpm for 20 minutes. After the discarding of the supernatant, the pellet is immersed in 10 mL of Tris buffer (20 mM Tris/500 mM NaCl (pH 7.9 at 4° C.)) and left undisturbed overnight.

(3-4) The solution obtained in the step (3-3) is desalted by dialysis (MWCO: 14000) at 4° C. An external solution in the dialysis is a Tris buffer.

(3-5) The resulting solution is purified with a Ni chelate column. His-Bind (Novagen) is used as a carrier to perform column purification at 4° C. according to the method recommended by the manufacturer.

(3-6) Dialysis for imidazole elimination is performed. A tube and external solution in the dialysis are the same as in the step (3-4).

When the obtained protein solution is confirmed by SDS-PAGE, a single band of approximately 6.5 kDa can be confirmed. This band is confirmed as DsbA-VH (G)-scFv (H) in the same way as in Example 4. This protein is confirmed to be a gold- and HEL-binding protein.

Example 7

Construction of β-Glucosidase-Fused Gold-Binding VH/HEL-Binding scFv Complex (1) Construction of Vector for expression of Gold-Binding VH/LacΔα-Fused Protein (1-1) Cloning of LacΔα Fragment The cloning of a LacΔα fragment can be performed with reference to the method for expression vector production described in Anal. Chem. (2002) 74, pp 2500-2504. The LacΔα is cloned from *E. coli* DH5α with the following primers:

```
LacΔα_fw:
                                    (SEQ ID NO: 105)
5'-CCCGGATCCGCGGCCGCCATGACCATGTTACGGAATTCACTGG-3'

LacΔα_bk
                                    (SEQ ID NO: 106)
5'-CCCCCCTCGAGTTATTTTTGACACCAGACCAACTGG-3'
```

(1-2) Insertion into pET-32

The obtained PCR fragment and a vector pET-32 (Novagen) are subjected to restriction enzyme reaction with NotI/XhoI according to the method recommended by the manufacturer. Gel purification is performed in the same way as above. The obtained PCR fragment and DNA fragment (approximately 5.9 kbp) are ligated with T4-Ligase (Roche).

(1-3) Insertion of Gold-Binding VH-Encoding DNA Fragment

The gold-binding VH is cleaved with NcoI/HindIII and inserted into the plasmid obtained in the step (1-2). The gold-binding VH-encoding DNA fragment is amplified by PCR in the same way as in Example 6. Primers used are described below. The obtained PCR fragment and plasmid are cleaved with restriction enzymes NcoI/HindIII and then ligated to construct a plasmid pET-GHΔα encoding trx-gold-binding VH-encoding DNA-LacΔα of interest.

```
7s4-fw-Nco1_2
ACATGCCATGGCAGGTGCAGTTGGTGGAGTCTG    (SEQ ID NO: 111)

HEL-bk-Hind3
AATGGCAAGCTTGGCCGTGATGATCAGCTTGGTA   (SEQ ID NO: 104)
```

(2) Construction of Vector for Expression of HEL-Binding scFv/LacΔω Fusion Protein (2-1) Cloning of LacΔω fragment The cloning of a LacΔω fragment can be performed with reference to the method for expression vector production described in Anal. Chem. (2002) 74, pp 2500-2504 in the same way as above. The LacAo is cloned from *E. coli* DH5α with the following primers:

```
LacΔω_fw
                                     (SEQ ID NO: 107)
5'-CCCGGATCCGCGGCCGCCATGACCATGATTACGGATTCACTGG-3'

LacΔω_bk
                                     (SEQ ID NO: 108)
5'-CCCCCCTCGAGTTACGGTGCACGGGTGAACTG-3'
```

(2-2) Insertion into pET-32

The obtained PCR fragment and a vector pET-32 (Novagen) are subjected to restriction enzyme reaction with NotI/XhoI according to the method recommended by the manufacturer. Gel purification is performed in the same way as above. The obtained PCR fragment and DNA fragment (approximately 5.9 kbp) are ligated with T4-Ligase (Roche).

(2-3) Insertion of HEL-Binding scFv-Encoding DNA Fragment

The DNA fragment coding HEL-binding scFv is cleaved with NcoI/HindIII and inserted into the plasmid obtained in the step (2-2). The DNA fragment coding HEL-binding scFv is amplified in the same way as in Example 6. The obtained PCR fragment and plasmid are cleaved with restriction enzymes NcoI/HindIII and then ligated to construct a plasmid pET-HFΔω encoding trx-HEL-binding scFv-encoding DNA-LacΔω of interest.

```
    scFv(HEL)_fw
                                     (SEQ ID NO: 109)
    5'-ACATGCCATGGGATATCGTCCTGACCCAGA-3' scFv(HEL)_bk
                                     (SEQ ID NO: 110)
    5'-AATGGCAAGCTTCGCGGAGACGGTGACGAGGGT-3'
```

(3) Fusion Protein Expression (3-1) Preculture

The plasmids were respectively used to express the proteins of interest in *E. coli* Origami B (DE3) pLysS (Novagen). Transformation is performed according to the method recommended by the manufacturer. The strains are developed onto a 2×YT plate (2×YT has the same composition as above and is supplemented with 15 g/L agar and further with 50 µg/mL ampicillin, 15 µg/mL kanamycin and 12.5 µg/mL tetracycline as antibiotics). A single colony obtained on the plate is cultured overnight at 37° C. in 5 mL of 2×YT solution (its composition is the same as above except for agar).

(3-2) Main Culture

The obtained culture solution (5 mL) is added to 400 mL of 2×YT medium of the same composition as above. At a time point of OD600=0.8 or more at 37° C., IPTG is added at the final concentration of 10 µM.

The culture is continued in an atmosphere at 16° C. for 12 hours.

(3-3) Collection of Protein a) Disruption of Bacterial Cells

The culture solution obtained in the step (3-2) is centrifuged at 6000 rpm for 30 minutes, and the supernatant is discarded. The pellet fraction, that is, cell fraction is suspended in 20 mL of phosphate buffer (2.7 mM KCl, 1.8 mM KHPO$_3$, 10 mM Na$_2$HPO$_3$ and 140 mM NaCl). Subsequently, French press is performed under conditions at 4° C. The obtained bacterial cell homogenate solution is centrifuged at 15000 rpm for 10 minutes to obtain a cytoplasm fraction solution.

b) Purification of Fusion Protein

All procedures described below are performed under an atmosphere at 4° C. The gold-binding VH-LacΔα-containing cytoplasm fraction solution and HEL-binding scFv-LacΔω-containing cytoplasm fraction solution thus obtained are mixed. The obtained mixture solution is purified by affinity column chromatography using NP-Sepharose (biosearchtech). The purification method follows the method recommended by the manufacturer. The eluted fraction is dialyzed with a phosphate buffer as an external solution. The external solution is replaced three times at 6-hour intervals.

(4) Confirmation of Double Binding Property of Fusion Protein

The fusion protein obtained in the step (3-3) is examined for its gold- and HEL-binding property in the same way as in Example 6 and confirmed to show a double binding property.

ADVANTAGES OF THE INVENTION

Advantages obtained by the present invention will be described below.

A target substance-capturing body of the present invention is characterized by comprising: a soluble protein used as a base; and two or more functional domains binding to different target substances. Thereby, since the soluble protein serves as a scaffold (base), the feature of being easily suspended or solubilized in an aqueous solution can be imparted to this target substance-capturing body. Furthermore, since the target substance-capturing body is composed of the functional domains respectively binding to different target substances, one molecule can capture two or more different molecules.

The target substance-capturing body of the present invention can be prepared as a protein complex composed of fusion proteins comprising the two or more different functional domains respectively fused with different soluble proteins. Since the target substance-capturing body is composed of such fusion proteins, the solubility of the soluble protein can be utilized effectively.

A soluble protein having a signal peptide or capable of functional addition of a signal peptide is adopted. Thereby, it is possible to produce the target substance-capturing body through a membrane transport process for producing the soluble protein in host cells and secreting it out of the cytoplasm. As a result, post-translational modification necessary to maintain stable protein three-dimensional structures such as disulfide bond formation can be performed in a production step in host bacterial cells.

Moreover, the soluble protein is a protein consisting of two or more constituent units. Furthermore, the two or more functional domains binding to different target substances may respectively be fused with the different constituent units. Thereby, it is possible to ease expression conditions of the fusion protein of the functional domain. Moreover, since plural constituent units derived from an identical protein have self-association ability, they can function as one molecule after association and result in no inconvenience for the capturing molecule.

Moreover, the soluble protein is selected from among phage coat proteins. Thereby, it is possible to stably display the target substance-capturing body on the phage surface without losing the desired functions of the different functional domains. Furthermore, the target substance-capturing body of interest can be obtained by a simple production method.

A functional domain that targets a substrate is included in the two or more functional domains comprised in the target substance-capturing body of the constitution described above. Thereby, it is possible to immobilize this target substance-capturing body in a particular orientation on the substrate. As a result, reduction in capturing ability, which is a problem presented by an immobilization method for conventional target substance-capturing bodies by physical adsorption or chemical crosslinking, can be suppressed.

A device of the present invention comprises the target substance-capturing body immobilized on a substrate, wherein a portion of the surface of the substrate used is composed of gold, and a functional domain having gold-binding ability is held in the target substance-capturing body. Thereby, it is possible to detect the binding between the target substance-capturing body and a target substance to be detected by not only the measurement of the quantity of scattered light but also optical measurement applying enhanced Raman and localized plasmon principles and electrical measurement utilizing its electrical properties. Furthermore, a method for detecting a target substance to be detected by use of the device comprising the target substance-capturing body and the substrate according to the present invention allows for the labeling of a probe or a target substance after reaction without introducing the label thereinto before the reaction as performed previously. As a result, reduction in the functions of labeled substances bound with labeling substances, which is a problem presented by conventional labeling methods, can be prevented. For example, reduction in the binding property between a target substance to be detected contained in a sample and its capturing molecule during reaction between the device and the sample due to the labeling of the target substance before the reaction can be prevented.

Furthermore, according to the method of the present invention, the scope of label selection can be expanded. Accordingly, the optimum label for a target substance can be selected. Thus, the present invention can provide a detection method and detection means capable of performing the reaction of the target substance/device according to the present invention/labeling substance at the same time or at an arbitrary time point.

INDUSTRIAL APPLICABILITY

The present invention provides a target substance-capturing body characterized by comprising a soluble protein and two or more functional domains binding to different target substances. The present invention further provides a device characterized by comprising a substrate bonded with a target substance-capturing body comprising the soluble protein, a functional domain having a substrate-binding property, and one or more functional domains binding to target substances different from the substrate. The present invention makes it possible to provide a technique for producing binding molecules (e.g., antibodies) highly specific to target substances at high yields and immobilizing the molecules with their activities maintained, which has conventionally presented a challenge to the industrial use of a target substance-capturing body.

This application claims priority from Japanese Patent Application No. 2005-192084 filed Jun. 30, 2005, which is hereby incorporated by reference herein.

The invention claimed is:

1. A device for capturing a target substance comprising:
a substrate; and
a target substance-capturing body comprising (i) a base comprising a soluble protein and (ii) two or more functional domains respectively capable of binding to different target substances,
wherein the two or more functional domains comprise a functional domain bound to the substrate and a functional domain for capturing a target substance different from the substrate, and
wherein at least a portion of the substrate contains gold, and
wherein the functional domain bound to the substrate is bound to the portion containing the gold and contains the amino acid sequence coded by SEQ ID NO: 80.

2. A detection instrument for detecting a target substance to be detected contained in an analyte comprising:
a device according to claim 1; and
detection means for detecting the binding of a target substance to a functional domain for capturing a target substance to be detected comprised in the device.

3. A kit for detecting a target substance to be detected contained in an analyte comprising:
a device according to claim 1; and
detection means for detecting the binding of a target substance to a functional domain for capturing a target substance to be detected comprised in the device.

4. A method for detecting a target substance to be detected in an analyte characterized by comprising the steps of:
reacting a device according to claim 1 with a target substance to be detected; and
detecting the binding of the target substance to be detected to a functional domain of the device.

5. A detecting method according to claim 4, further comprising the step of preparing the device by reacting the target substance-capturing body with the substrate to bind the target substance-capturing body to the substrate.

* * * * *

SEQUENCE LISTING

```
<160> NUMBER OF SEQ ID NOS: 113

<210> SEQ ID NO 1
<211> LENGTH: 5
<212> TYPE: PRT
<213> ORGANISM: Homo sapiens

<400> SEQUENCE: 1

Asp Tyr Tyr Met Asp
1               5

<210> SEQ ID NO 2
<211> LENGTH: 17
<212> TYPE: PRT
<213> ORGANISM: Homo sapiens

<400> SEQUENCE: 2

Ser Ile Lys Gln Asp Gly Ser Glu Thr Arg Tyr Gly Asp Ser Val Arg
1               5                   10                  15

Gly
```

```
<210> SEQ ID NO 3
<211> LENGTH: 9
<212> TYPE: PRT
<213> ORGANISM: Homo sapiens

<400> SEQUENCE: 3

Glu Leu Asp Gly Gly Phe Phe Asp Phe
1               5

<210> SEQ ID NO 4
<211> LENGTH: 5
<212> TYPE: PRT
<213> ORGANISM: Homo sapiens

<400> SEQUENCE: 4

Gly His Trp Met His
1               5

<210> SEQ ID NO 5
<211> LENGTH: 17
<212> TYPE: PRT
<213> ORGANISM: Homo sapiens

<400> SEQUENCE: 5

Arg Ile Asp Glu His Gly Ser Ser Ala Tyr Tyr Ala Asp Ser Val Asn
1               5                   10                  15
Gly

<210> SEQ ID NO 6
<211> LENGTH: 15
<212> TYPE: PRT
<213> ORGANISM: Homo sapiens

<400> SEQUENCE: 6

Leu Gly Phe Ile Thr Pro Glu Val Val His Trp Ser Ser Asp Ile
1               5                   10                  15

<210> SEQ ID NO 7
<211> LENGTH: 5
<212> TYPE: PRT
<213> ORGANISM: Homo sapiens

<400> SEQUENCE: 7

Arg Phe Tyr Trp Asn
1               5

<210> SEQ ID NO 8
<211> LENGTH: 16
<212> TYPE: PRT
<213> ORGANISM: Homo sapiens

<400> SEQUENCE: 8

Arg Ile Phe Thr Asn Gly Thr Thr Asn Tyr Asn Pro Ser Leu Gly Ser
1               5                   10                  15

<210> SEQ ID NO 9
<211> LENGTH: 13
<212> TYPE: PRT
<213> ORGANISM: Homo sapiens

<400> SEQUENCE: 9

Gly Gly Asp Tyr Gly Pro Ala Leu Ala Trp Phe Asp Pro
1               5                   10
```

```
<210> SEQ ID NO 10
<211> LENGTH: 10
<212> TYPE: PRT
<213> ORGANISM: Homo sapiens

<400> SEQUENCE: 10

Glu Ser Met Val Arg Asp Gly Met Asp Val
1               5                   10

<210> SEQ ID NO 11
<211> LENGTH: 5
<212> TYPE: PRT
<213> ORGANISM: Homo sapiens

<400> SEQUENCE: 11

Gly Tyr Tyr Trp Thr
1               5

<210> SEQ ID NO 12
<211> LENGTH: 16
<212> TYPE: PRT
<213> ORGANISM: Homo sapiens

<400> SEQUENCE: 12

Asp Ser Ser His Ser Gly Arg Thr Asn Tyr Asn Pro Ser Leu Lys Ser
1               5                   10                  15

<210> SEQ ID NO 13
<211> LENGTH: 9
<212> TYPE: PRT
<213> ORGANISM: Homo sapiens

<400> SEQUENCE: 13

Ala Glu Glu Thr Val Thr Ile Val Pro
1               5

<210> SEQ ID NO 14
<211> LENGTH: 5
<212> TYPE: PRT
<213> ORGANISM: Homo sapiens

<400> SEQUENCE: 14

Ser His Tyr Ile His
1               5

<210> SEQ ID NO 15
<211> LENGTH: 17
<212> TYPE: PRT
<213> ORGANISM: Homo sapiens

<400> SEQUENCE: 15

Gly Phe Ile Pro Ile Phe Gly Thr Ser Asn Tyr Ala Glu Lys Phe Lys
1               5                   10                  15

Gly

<210> SEQ ID NO 16
<211> LENGTH: 15
<212> TYPE: PRT
<213> ORGANISM: Homo sapiens

<400> SEQUENCE: 16

Pro Arg Arg Ser Ser Ser Ser Lys Thr Phe Ser Ala Leu Asp Tyr
1               5                   10                  15
```

```
<210> SEQ ID NO 17
<211> LENGTH: 5
<212> TYPE: PRT
<213> ORGANISM: Homo sapiens

<400> SEQUENCE: 17

Asp Tyr Ala Met Asn
1               5

<210> SEQ ID NO 18
<211> LENGTH: 15
<212> TYPE: PRT
<213> ORGANISM: Homo sapiens

<400> SEQUENCE: 18

Phe Ile Arg Ser Arg Gly Phe Gly Gly Thr Pro Glu Tyr Ala Ala
1               5                   10                  15

<210> SEQ ID NO 19
<211> LENGTH: 18
<212> TYPE: PRT
<213> ORGANISM: Homo sapiens

<400> SEQUENCE: 19

Asp Tyr Arg Pro Leu Gln Phe Trp Pro Gly Arg Gln Met Asp Ala Phe
1               5                   10                  15

Asp Ile

<210> SEQ ID NO 20
<211> LENGTH: 5
<212> TYPE: PRT
<213> ORGANISM: Homo sapiens

<400> SEQUENCE: 20

Ser Tyr Trp Ile Asn
1               5

<210> SEQ ID NO 21
<211> LENGTH: 17
<212> TYPE: PRT
<213> ORGANISM: Homo sapiens

<400> SEQUENCE: 21

Met Ile Tyr Pro Ala Asp Ser Asp Thr Arg Tyr Ser Pro Ser Phe Gln
1               5                   10                  15

Gly

<210> SEQ ID NO 22
<211> LENGTH: 10
<212> TYPE: PRT
<213> ORGANISM: Homo sapiens

<400> SEQUENCE: 22

Leu Gly Ile Gly Gly Arg Tyr Met Ser Arg
1               5                   10

<210> SEQ ID NO 23
<211> LENGTH: 5
<212> TYPE: PRT
<213> ORGANISM: Homo sapiens

<400> SEQUENCE: 23

Arg Tyr Tyr Ile His
1               5
```

<210> SEQ ID NO 24
<211> LENGTH: 17
<212> TYPE: PRT
<213> ORGANISM: Homo sapiens

<400> SEQUENCE: 24

Met Ile Asn Pro Arg Gly Gly Ser Thr Thr Tyr Ala Gln Lys Phe Gln
1               5                   10                  15
Gly

<210> SEQ ID NO 25
<211> LENGTH: 14
<212> TYPE: PRT
<213> ORGANISM: Homo sapiens

<400> SEQUENCE: 25

Glu Ser Met Pro Gly Arg Asp Val Arg Asp Gly Met Asp Val
1               5                   10

<210> SEQ ID NO 26
<211> LENGTH: 5
<212> TYPE: PRT
<213> ORGANISM: Homo sapiens

<400> SEQUENCE: 26

Asp His Tyr Ile His
1               5

<210> SEQ ID NO 27
<211> LENGTH: 14
<212> TYPE: PRT
<213> ORGANISM: Homo sapiens

<400> SEQUENCE: 27

Pro Asn Ser Gly Ala Thr Lys Tyr Ala Gln Lys Phe His Gly
1               5                   10

<210> SEQ ID NO 28
<211> LENGTH: 9
<212> TYPE: PRT
<213> ORGANISM: Homo sapiens

<400> SEQUENCE: 28

Gly Ile Leu Leu Ala Arg Leu Asp Val
1               5

<210> SEQ ID NO 29
<211> LENGTH: 5
<212> TYPE: PRT
<213> ORGANISM: Homo sapiens

<400> SEQUENCE: 29

Asn Tyr Ala Ile Ser
1               5

<210> SEQ ID NO 30
<211> LENGTH: 17
<212> TYPE: PRT
<213> ORGANISM: Homo sapiens

<400> SEQUENCE: 30

Gly Thr Leu Leu Met Leu Arg Ile Ile Asn Ser Ala Gln Lys Phe Gln
1               5                   10                  15
Gly

```
<210> SEQ ID NO 31
<211> LENGTH: 14
<212> TYPE: PRT
<213> ORGANISM: Homo sapiens

<400> SEQUENCE: 31

Ala Leu Pro Thr Ser Leu Gly Pro Ile Gly Tyr Leu His His
1               5                   10

<210> SEQ ID NO 32
<211> LENGTH: 5
<212> TYPE: PRT
<213> ORGANISM: Homo sapiens

<400> SEQUENCE: 32

Asp Tyr Tyr Met His
1               5

<210> SEQ ID NO 33
<211> LENGTH: 17
<212> TYPE: PRT
<213> ORGANISM: Homo sapiens

<400> SEQUENCE: 33

Trp Ile Asn Pro Asn Ile Gly Ala Thr Asn His Ala Gln Arg Phe Gln
1               5                   10                  15

Gly

<210> SEQ ID NO 34
<211> LENGTH: 9
<212> TYPE: PRT
<213> ORGANISM: Homo sapiens

<400> SEQUENCE: 34

Asp Leu Gly Ile Ser Ala Phe Glu Asn
1               5

<210> SEQ ID NO 35
<211> LENGTH: 5
<212> TYPE: PRT
<213> ORGANISM: Homo sapiens

<400> SEQUENCE: 35

Asp Tyr Phe Met His
1               5

<210> SEQ ID NO 36
<211> LENGTH: 17
<212> TYPE: PRT
<213> ORGANISM: Homo sapiens

<400> SEQUENCE: 36

Trp Ile Asn Pro Asn Ser Gly Val Thr His Tyr Ala Gln Lys Phe Gln
1               5                   10                  15

Gly

<210> SEQ ID NO 37
<211> LENGTH: 12
<212> TYPE: PRT
<213> ORGANISM: Homo sapiens

<400> SEQUENCE: 37

Glu Leu Ile Thr Gly Arg Leu Pro Thr Asp Asn Asp
1               5                   10
```

<210> SEQ ID NO 38
<211> LENGTH: 5
<212> TYPE: PRT
<213> ORGANISM: Homo sapiens

<400> SEQUENCE: 38

Gly Tyr Tyr Ile His
1               5

<210> SEQ ID NO 39
<211> LENGTH: 17
<212> TYPE: PRT
<213> ORGANISM: Homo sapiens

<400> SEQUENCE: 39

Trp Ile Asn Pro Asn Thr Gly Gly Thr Asn Tyr Ala Gln Lys Phe Gln
1               5                   10                  15

Gly

<210> SEQ ID NO 40
<211> LENGTH: 18
<212> TYPE: PRT
<213> ORGANISM: Homo sapiens

<400> SEQUENCE: 40

Arg Ser Gly Gly Ser Gly Arg Tyr Trp Gly Ile Lys Asn Asn Trp Phe
1               5                   10                  15

Asp Pro

<210> SEQ ID NO 41
<211> LENGTH: 17
<212> TYPE: PRT
<213> ORGANISM: Homo sapiens

<400> SEQUENCE: 41

Trp Ile Asn Pro Asn Ser Gly Val Thr His Tyr Ala Gln Lys Phe Gln
1               5                   10                  15

Gly

<210> SEQ ID NO 42
<211> LENGTH: 12
<212> TYPE: PRT
<213> ORGANISM: Homo sapiens

<400> SEQUENCE: 42

Glu Leu Ile Ala Gly Arg Leu Pro Thr Asp Asn Asp
1               5                   10

<210> SEQ ID NO 43
<211> LENGTH: 5
<212> TYPE: PRT
<213> ORGANISM: Homo sapiens

<400> SEQUENCE: 43

Asp Tyr Tyr Phe His
1               5

<210> SEQ ID NO 44
<211> LENGTH: 17
<212> TYPE: PRT
<213> ORGANISM: Homo sapiens

```
<400> SEQUENCE: 44

Trp Ile Asn Phe Asp Ser Gly Gly Thr Asn Tyr Ala Gln Lys Phe Gln
1               5                   10                  15
Gly

<210> SEQ ID NO 45
<211> LENGTH: 13
<212> TYPE: PRT
<213> ORGANISM: Homo sapiens

<400> SEQUENCE: 45

Gly Ser Arg Tyr Asn Ser Gly Trp Tyr Tyr Phe Asp Tyr
1               5                   10

<210> SEQ ID NO 46
<211> LENGTH: 5
<212> TYPE: PRT
<213> ORGANISM: Homo sapiens

<400> SEQUENCE: 46

Ile Ser Ser Pro Thr
1               5

<210> SEQ ID NO 47
<211> LENGTH: 16
<212> TYPE: PRT
<213> ORGANISM: Homo sapiens

<400> SEQUENCE: 47

Glu Ile Tyr His Ser Gly Thr Ser His His Asn Pro Ser Leu Lys Asn
1               5                   10                  15

<210> SEQ ID NO 48
<211> LENGTH: 11
<212> TYPE: PRT
<213> ORGANISM: Homo sapiens

<400> SEQUENCE: 48

Leu Asp Phe Asp Ser Pro Leu Gly Met Asp Ala
1               5                   10

<210> SEQ ID NO 49
<211> LENGTH: 11
<212> TYPE: PRT
<213> ORGANISM: Homo sapiens

<400> SEQUENCE: 49

Arg Ala Ser Gln Ser Ile Ser Thr Tyr Leu Asn
1               5                   10

<210> SEQ ID NO 50
<211> LENGTH: 7
<212> TYPE: PRT
<213> ORGANISM: Homo sapiens

<400> SEQUENCE: 50

Ala Ala Ser Ser Leu Gln Ser
1               5

<210> SEQ ID NO 51
<211> LENGTH: 9
<212> TYPE: PRT
```

```
<400> SEQUENCE: 51

Gln Gln Ser Tyr Ser Thr Pro Arg Thr
1               5

<210> SEQ ID NO 52
<211> LENGTH: 11
<212> TYPE: PRT
<213> ORGANISM: Homo sapiens

<400> SEQUENCE: 52

Arg Ala Ser Glu Asp Val Asn Ser Trp Leu Ala
1               5                   10

<210> SEQ ID NO 53
<211> LENGTH: 7
<212> TYPE: PRT
<213> ORGANISM: Homo sapiens

<400> SEQUENCE: 53

Gly Ser Thr Asn Leu Gln Gly
1               5

<210> SEQ ID NO 54
<211> LENGTH: 10
<212> TYPE: PRT
<213> ORGANISM: Homo sapiens

<400> SEQUENCE: 54

Lys Tyr Phe Asp Ala Leu Pro Pro Val Thr
1               5                   10

<210> SEQ ID NO 55
<211> LENGTH: 17
<212> TYPE: PRT
<213> ORGANISM: Homo sapiens

<400> SEQUENCE: 55

Thr Ser Ser Gln Ser Leu Leu Tyr Thr Ser Asn Asn Lys Asn Tyr Leu
1               5                   10                  15

Thr

<210> SEQ ID NO 56
<211> LENGTH: 7
<212> TYPE: PRT
<213> ORGANISM: Homo sapiens

<400> SEQUENCE: 56

Trp Ala Ser Thr Arg Glu Phe
1               5

<210> SEQ ID NO 57
<211> LENGTH: 9
<212> TYPE: PRT
<213> ORGANISM: Homo sapiens

<400> SEQUENCE: 57

Gln Gln Tyr Ser Asp Pro Pro Pro Thr
1               5

<210> SEQ ID NO 58
<211> LENGTH: 124
<212> TYPE: PRT
<213> ORGANISM: Homo sapiens
```

<400> SEQUENCE: 58

```
Glu Val Gln Val Val Glu Ser Gly Ala Glu Val Lys Lys Pro Gly Ala
1               5                   10                  15

Ser Val Lys Val Ser Cys Lys Ala Ser Gly Tyr Thr Phe Asn Ser His
            20                  25                  30

Tyr Ile His Trp Val Arg Gln Ala Pro Gly Gln Gly Leu Glu Trp Met
        35                  40                  45

Gly Gly Phe Ile Pro Ile Phe Gly Thr Ser Asn Tyr Ala Glu Lys Phe
    50                  55                  60

Lys Gly Arg Val Thr Phe Thr Val Asp Thr Ser Thr Asn Thr Ala His
65                  70                  75                  80

Met Glu Leu Thr Arg Leu Arg Ser Glu Asp Thr Ala Ile Tyr Tyr Cys
                85                  90                  95

Ala Leu Pro Arg Arg Ser Ser Ser Lys Thr Phe Ser Ala Leu Asp
            100                 105                 110

Tyr Trp Gly Gln Gly Thr Leu Val Thr Val Ser Ser
        115                 120
```

<210> SEQ ID NO 59
<211> LENGTH: 129
<212> TYPE: PRT
<213> ORGANISM: Homo sapiens

<400> SEQUENCE: 59

```
Gln Val Gln Leu Thr Glu Ser Gly Gly Gly Leu Val Gln Pro Gly Arg
1               5                   10                  15

Ser Leu Arg Leu Ser Cys Thr Ala Ser Gly Phe Thr Leu Gly Asp Tyr
            20                  25                  30

Ala Met Asn Trp Val Arg Gln Ala Pro Gly Lys Gly Leu Glu Trp Val
        35                  40                  45

Gly Phe Ile Arg Ser Arg Gly Phe Gly Gly Thr Pro Glu Tyr Ala Ala
    50                  55                  60

Ser Val Lys Gly Arg Phe Thr Ile Ser Arg Asp Asn Ser Lys Gly Ile
65                  70                  75                  80

Ala Tyr Leu Glu Met Asn Ser Leu Lys Thr Glu Asp Thr Ala Met Tyr
                85                  90                  95

Tyr Cys Thr Arg Asp Tyr Arg Pro Leu Gln Phe Trp Pro Gly Arg Gln
            100                 105                 110

Met Asp Ala Phe Asp Ile Trp Gly Gln Gly Thr Met Val Thr Val Ser
        115                 120                 125

Ser
```

<210> SEQ ID NO 60
<211> LENGTH: 120
<212> TYPE: PRT
<213> ORGANISM: Homo sapiens

<400> SEQUENCE: 60

```
Gln Val Gln Leu Val Glu Ser Gly Ala Glu Val Lys Lys Ala Gly Glu
1               5                   10                  15

Ser Leu Lys Ile Ser Cys Lys Gly Ser Gly Tyr Ser Phe Pro Ser Tyr
            20                  25                  30

Trp Ile Asn Trp Val Arg Gln Met Pro Gly Lys Gly Leu Glu Trp Met
        35                  40                  45

Gly Met Ile Tyr Pro Ala Asp Ser Asp Thr Arg Tyr Ser Pro Ser Phe
    50                  55                  60
```

```
Gln Gly His Val Thr Ile Ser Ala Asp Lys Ser Ile Asn Thr Ala Tyr
 65                  70                  75                  80

Leu Gln Trp Ala Gly Leu Lys Ala Ser Asp Thr Ala Ile Tyr Tyr Cys
                 85                  90                  95

Ala Arg Leu Gly Ile Gly Gly Arg Tyr Met Ser Arg Trp Gly Gln Gly
            100                 105                 110

Thr Leu Val Thr Val Ser Ser Ala
        115                 120

<210> SEQ ID NO 61
<211> LENGTH: 119
<212> TYPE: PRT
<213> ORGANISM: Homo sapiens

<400> SEQUENCE: 61

Gln Val Gln Leu Val Gln Ser Gly Ala Glu Val Lys Lys Pro Gly Ala
 1               5                  10                  15

Ser Val Lys Val Ser Cys Glu Ala Ser Gly Tyr Thr Phe Thr Arg Tyr
                20                  25                  30

Tyr Ile His Trp Val Arg Gln Ala Pro Gly Gln Gly Leu Glu Trp Met
            35                  40                  45

Gly Met Ile Asn Pro Arg Gly Gly Ser Thr Thr Tyr Ala Gln Lys Phe
         50                 55                  60

Gln Gly Arg Val Thr Met Thr Arg Asp Arg Ser Thr Ser Thr Val His
 65                  70                  75                  80

Met Glu Val Ser Ser Leu Arg Ser Asp Asp Thr Ala Val Tyr Tyr Cys
                 85                  90                  95

Ala Arg Glu Ser Met Val Arg Asp Gly Met Asp Val Trp Gly Gln Gly
            100                 105                 110

Thr Thr Val Thr Val Ser Ser
        115

<210> SEQ ID NO 62
<211> LENGTH: 118
<212> TYPE: PRT
<213> ORGANISM: Homo sapiens

<400> SEQUENCE: 62

Glu Val Gln Leu Val Gln Ser Gly Ser Glu Val Lys Lys Pro Gly Ala
 1               5                  10                  15

Ser Leu Lys Val Ser Cys Lys Ala Ser Gly Tyr Ser Phe Val Asp His
                20                  25                  30

Tyr Ile His Trp Val Arg Gln Ala Pro Gly Gln Gly Leu Glu Trp Met
            35                  40                  45

Gly Trp Leu Asn Pro Asn Ser Gly Ala Thr Lys Tyr Ala Gln Lys Phe
         50                 55                  60

His Gly Arg Val Thr Leu Thr Arg Asp Thr Ser Ile Ser Thr Val Tyr
 65                  70                  75                  80

Met Glu Leu Ser Arg Leu Ile Ser Asp Asp Thr Ala Val Tyr Phe Cys
                 85                  90                  95

Ala Arg Gly Ile Leu Leu Ala Arg Leu Asp Val Trp Gly Gln Gly Thr
            100                 105                 110

Leu Val Thr Val Ser Ser
        115
```

```
<210> SEQ ID NO 63
<211> LENGTH: 118
<212> TYPE: PRT
<213> ORGANISM: Homo sapiens

<400> SEQUENCE: 63

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Asp Trp Val Arg Gln Ala Pro Gly Lys Gly Leu Gln Trp Val
        35                  40                  45

Ala Ser Ile Lys Gln Asp Gly Ser Glu Thr Arg Tyr Gly Asp Ser Val
    50                  55                  60

Arg Gly Arg Phe Ile Ile Ser Arg Asp Asn Thr Lys Asn Ser Ala Tyr
65                  70                  75                  80

Leu Gln Met Asn Thr Leu Ser Ala Glu Asp Arg Ala Val Tyr His Cys
                85                  90                  95

Val Arg Glu Leu Asp Gly Gly Phe Phe Asp Phe Trp Gly Gln Gly Thr
            100                 105                 110

Leu Val Thr Val Ser Ser
        115

<210> SEQ ID NO 64
<211> LENGTH: 121
<212> TYPE: PRT
<213> ORGANISM: Homo sapiens

<400> SEQUENCE: 64

Gln Val Gln Leu Gln Glu Ser Gly Pro Gly Leu Val Lys Pro Ser Glu
1               5                   10                  15

Thr Leu Ser Leu Thr Cys Ser Val Ser Gly Ala Ser Met Ser Arg Phe
            20                  25                  30

Tyr Trp Asn Trp Ile Arg His Ser Ala Gly Lys Gly Leu Glu Trp Ile
        35                  40                  45

Gly Arg Ile Phe Thr Asn Gly Thr Thr Asn Tyr Asn Pro Ser Leu Gly
    50                  55                  60

Ser Arg Val Thr Met Ser Val Asp Thr Ala Lys Asn Gln Phe Ser Leu
65                  70                  75                  80

Arg Val Thr Ser Val Thr Ala Ala Asp Ala Ala Val Tyr Tyr Cys Ala
                85                  90                  95

Arg Gly Gly Asp Tyr Gly Pro Ala Leu Ala Trp Phe Asp Pro Trp Gly
            100                 105                 110

Gln Gly Thr Leu Val Thr Val Ser Ser
        115                 120

<210> SEQ ID NO 65
<211> LENGTH: 124
<212> TYPE: PRT
<213> ORGANISM: Homo sapiens

<400> SEQUENCE: 65

Gln Val Gln Leu Gln Glu Trp Gly Gly Gly Val Val Gln Pro Gly Arg
1               5                   10                  15

Ser Leu Arg Leu Ser Cys Val Ala Ser Gly Phe Thr Phe Ser Gly His
            20                  25                  30

Trp Met His Trp Val Arg Gln Ala Pro Gly Lys Gly Leu Val Trp Val
        35                  40                  45
```

```
Ser Arg Ile Asp Glu His Gly Ser Ala Tyr Tyr Ala Asp Ser Val
    50                  55                  60

Asn Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Phe Ile Thr Pro Glu Val Val His Trp Ser Ser Asp
                100                 105                 110

Ile Trp Gly Gln Gly Thr Met Val Thr Val Ser Ser
            115                 120

<210> SEQ ID NO 66
<211> LENGTH: 119
<212> TYPE: PRT
<213> ORGANISM: Homo sapiens

<400> SEQUENCE: 66

Gln Val Gln Leu Val Gln Ser Gly Ala Glu Val Lys Lys Pro Gly Ala
1               5                   10                  15

Ser Val Lys Val Ser Cys Glu Ala Ser Gly Tyr Thr Phe Thr Arg Tyr
                20                  25                  30

Tyr Ile His Trp Val Arg Gln Ala Pro Gly Gln Gly Leu Glu Trp Met
            35                  40                  45

Gly Met Ile Asn Pro Arg Gly Gly Ser Thr Thr Tyr Ala Gln Lys Phe
        50                  55                  60

Gln Gly Arg Val Thr Met Thr Arg Asp Arg Ser Thr Ser Thr Val His
65                  70                  75                  80

Met Glu Val Ser Ser Leu Arg Ser Asp Asp Thr Ala Val Tyr Tyr Cys
                85                  90                  95

Ala Arg Glu Ser Met Val Arg Asp Gly Met Asp Val Trp Gly Gln Gly
                100                 105                 110

Thr Thr Val Thr Val Ser Ser
            115

<210> SEQ ID NO 67
<211> LENGTH: 128
<212> TYPE: PRT
<213> ORGANISM: Homo sapiens

<400> SEQUENCE: 67

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Thr Trp Ile Arg Gln Pro Pro Gly Lys Gly Leu Glu Trp Ile
            35                  40                  45

Gly Asp Ser Ser His Ser Gly Arg Thr Asn Tyr Asn Pro Ser Leu Lys
        50                  55                  60

Ser Arg Val Thr Ile Ser Val Asp Ala Ser Lys Lys Gln Phe Ser Leu
65                  70                  75                  80

Lys Leu Ile Ser Val Thr Ala Ala Glu Pro Phe Arg Ser Ser Ser Glu
                85                  90                  95

Met Ser Phe Cys Ser Leu Ala Glu Glu Thr Val Thr Ile Val Pro Trp
                100                 105                 110

Pro Gln Thr Ser Lys Ala Pro Pro Asn Arg Pro Arg Cys Phe Val Ser
            115                 120                 125
```

<210> SEQ ID NO 68
<211> LENGTH: 125
<212> TYPE: PRT
<213> ORGANISM: Homo sapiens

<400> SEQUENCE: 68

```
Gly Ala Ala Gly Glu Ser Gly Ala Glu Val Arg Lys Pro Gly Ser Ser
1               5                   10                  15

Val Lys Val Ser Cys Lys Ala Ser Gly Gly Ser Ile Asn Asn Tyr Ala
            20                  25                  30

Ile Ser Trp Val Arg Gln Ala Pro Gly Gln Gly Leu Glu Trp Ile Gly
        35                  40                  45

Gly Thr Leu Leu Met Leu Arg Ile Ile Asn Ser Ala Gln Lys Phe Gln
    50                  55                  60

Gly Arg Val Ser Ile Thr Ala Asp Thr Ser Thr Asn Thr Ala Tyr Met
65                  70                  75                  80

Glu Leu Ser Ser Leu Arg Ser Glu Asp Thr Ala Met Tyr Tyr Cys Ala
                85                  90                  95

Ser Ser Val Ala Ala Leu Pro Thr Ser Leu Gly Pro Ile Gly Tyr Leu
            100                 105                 110

His His Trp Gly Gln Gly Thr Leu Val Thr Val Ser Ser
        115                 120                 125
```

<210> SEQ ID NO 69
<211> LENGTH: 117
<212> TYPE: PRT
<213> ORGANISM: Homo sapiens

<400> SEQUENCE: 69

```
Gly Ala Gly Gly Glu Ser Gly Ala Asp Val Lys Lys Pro Gly Ala Ser
1               5                   10                  15

Val Lys Val Ser Cys Lys Ala Ser Gly Tyr Thr Phe Thr Asp Tyr Tyr
            20                  25                  30

Met His Trp Val Arg Gln Ala Pro Gly Gln Gly Leu Glu Trp Met Gly
        35                  40                  45

Trp Ile Asn Pro Asn Ile Gly Ala Thr Asn His Ala Gln Arg Phe Gln
    50                  55                  60

Gly Arg Leu Thr Val Ser Arg Asp Thr Ser Ile Thr Thr Val Tyr Met
65                  70                  75                  80

Glu Leu Ser Arg Leu Gln Ser Asp Asp Thr Ala Val Tyr Phe Cys Ala
                85                  90                  95

Arg Asp Leu Gly Ile Ser Ala Phe Glu Asn Trp Gly Gln Gly Thr Met
            100                 105                 110

Val Thr Val Ser Ser
        115
```

<210> SEQ ID NO 70
<211> LENGTH: 120
<212> TYPE: PRT
<213> ORGANISM: Homo sapiens

<400> SEQUENCE: 70

```
Gly Asp Gly Gly Glu Ser Gly Ala Glu Val Arg Lys Pro Gly Ala Ser
1               5                   10                  15

Val Lys Val Ser Cys Lys Ala Ser Arg Tyr Ser Phe Thr Asp Tyr Phe
            20                  25                  30

Met His Trp Val Arg Gln Ala Pro Gly Gln Gly Leu Glu Trp Met Gly
        35                  40                  45
```

```
Trp Ile Asn Pro Asn Ser Gly Val Thr His Tyr Ala Gln Lys Phe Gln
         50                  55                  60

Gly Arg Val Thr Met Thr Arg Asp Thr Ser Ile Asn Thr Ala Tyr Met
 65                  70                  75                  80

Glu Val Ser Arg Leu Arg Tyr Asp Asp Thr Ala Val Tyr Tyr Cys Thr
                 85                  90                  95

Arg Glu Leu Ile Thr Gly Arg Leu Pro Thr Asp Asn Asp Trp Gly Gln
             100                 105                 110

Gly Thr Leu Val Thr Val Ser Ser
             115                 120

<210> SEQ ID NO 71
<211> LENGTH: 126
<212> TYPE: PRT
<213> ORGANISM: Homo sapiens

<400> SEQUENCE: 71

Gly Ala Ala Gly Glu Ser Gly Ala Glu Val Arg Lys Pro Gly Ala Ser
 1               5                  10                  15

Val Lys Val Ser Cys Lys Thr Ser Gly Tyr Asn Phe Arg Gly Tyr Tyr
                 20                  25                  30

Ile His Trp Val Arg Gln Ala Pro Gly Gln Gly Leu Glu Trp Met Gly
             35                  40                  45

Trp Ile Asn Pro Asn Thr Gly Thr Asn Tyr Ala Gln Lys Phe Gln
         50                  55                  60

Gly Arg Val Thr Met Thr Arg Asp Thr Ser Ile Asn Thr Ala Tyr Met
 65                  70                  75                  80

Glu Val Ser Lys Leu Arg Ser Asp Asp Thr Ala Val Tyr Tyr Cys Ala
                 85                  90                  95

Arg Arg Ser Gly Gly Ser Gly Arg Tyr Trp Gly Ile Lys Asn Asn Trp
             100                 105                 110

Phe Asp Pro Trp Gly Gln Gly Thr Leu Val Thr Val Ser Ser
             115                 120                 125

<210> SEQ ID NO 72
<211> LENGTH: 120
<212> TYPE: PRT
<213> ORGANISM: Homo sapiens

<400> SEQUENCE: 72

Gly Asp Gly Gly Glu Ser Gly Ala Glu Val Arg Lys Pro Gly Ala Ser
 1               5                  10                  15

Val Lys Val Ser Cys Lys Ala Ser Arg Tyr Ser Phe Thr Asp Tyr Phe
                 20                  25                  30

Met His Trp Val Arg Gln Ala Pro Gly Gln Gly Leu Glu Trp Met Gly
             35                  40                  45

Trp Ile Asn Pro Asn Ser Gly Val Thr His Tyr Ala Gln Lys Phe Gln
         50                  55                  60

Gly Arg Val Thr Met Thr Arg Asp Thr Ser Ile Asn Thr Ala Tyr Met
 65                  70                  75                  80

Glu Val Ser Arg Leu Arg Tyr Asp Asp Thr Ala Val Tyr Tyr Cys Thr
                 85                  90                  95

Arg Glu Leu Ile Ala Gly Arg Leu Pro Thr Asp Asn Asp Trp Gly Gln
             100                 105                 110

Gly Thr Leu Val Thr Val Ser Ser
             115                 120
```

<210> SEQ ID NO 73
<211> LENGTH: 122
<212> TYPE: PRT
<213> ORGANISM: Homo sapiens

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ala Gly Tyr Thr Phe Thr Asp Tyr
            20                  25                  30

Tyr Phe His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Asp Leu Ser Arg Leu Arg Ser Asp Asp Thr Ala Val Cys Tyr Cys
                85                  90                  95

Ala Arg Gly Ser Arg Tyr Asn Ser Gly Trp Tyr Tyr Phe Asp Tyr Trp
            100                 105                 110

Ser Arg Gly Thr Leu Val Thr Val Ser Ser
        115                 120

<210> SEQ ID NO 74
<211> LENGTH: 120
<212> TYPE: PRT
<213> ORGANISM: Homo sapiens

<400> SEQUENCE: 74

Gln Val Gln Leu Gln Glu Trp Gly Pro Gly Leu Val Lys Pro Ser Gly
1               5                   10                  15

Thr Leu Ser Leu Thr Cys Ala Val Ser Gly Gly Thr Ile Ser Ser Pro
            20                  25                  30

Thr Trp Trp Asn Trp Val Arg Gln Pro Pro Gly Lys Gly Leu Glu Trp
        35                  40                  45

Ile Gly Glu Ile Tyr His Ser Gly Thr Ser His Asn Pro Ser Leu
    50                  55                  60

Lys Asn Arg Val Thr Leu Ser Val Asp Lys Ser Lys Asn Gln Phe Ser
65                  70                  75                  80

Leu Lys Leu Asn Ser Met Thr Ala Ala Asp Thr Ala Val Tyr Phe Cys
                85                  90                  95

Thr Arg Leu Asp Phe Asp Ser Pro Leu Gly Met Asp Ala Trp Gly Gln
            100                 105                 110

Gly Thr Thr Val Thr Val Ser Ser
        115                 120

<210> SEQ ID NO 75
<211> LENGTH: 109
<212> TYPE: PRT
<213> ORGANISM: Homo sapiens

<400> SEQUENCE: 75

Asp Ile Val Met Thr Arg Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Ala Gly Lys Ala Pro Lys Leu Leu Ile
        35                  40                  45

```
Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Arg
                 85                  90                  95

Thr Phe Gly Gln Gly Thr Lys Val Glu Ile Lys Arg Ala
            100                 105

<210> SEQ ID NO 76
<211> LENGTH: 110
<212> TYPE: PRT
<213> ORGANISM: Homo sapiens

<400> SEQUENCE: 76

Glu Ile Val Leu Thr Gln Ser Pro Ser Ser Val Ser Ala Ser Val Gly
 1               5                  10                  15

Asp Arg Val Thr Ile Thr Cys Arg Ala Ser Glu Asp Val Asn Ser Trp
             20                  25                  30

Leu Ala Trp Tyr Gln Gln Lys Pro Gly Lys Ala Pro Lys Leu Leu Ile
         35                  40                  45

Tyr Gly Ser Thr Asn Leu Gln Gly Gly Val Pro Ser Arg Phe Ser Gly
     50                  55                  60

Arg Gly Ser Gly Thr His Phe Thr Phe Thr Ile Asn Gly Leu Gln Pro
 65                  70                  75                  80

Glu Asp Ile Ala Thr Tyr Tyr Cys Lys Tyr Phe Asp Ala Leu Pro Pro
                 85                  90                  95

Val Thr Phe Gly Gln Gly Thr Arg Leu Glu Ile Lys Arg Ala
            100                 105                 110

<210> SEQ ID NO 77
<211> LENGTH: 115
<212> TYPE: PRT
<213> ORGANISM: Homo sapiens

<400> SEQUENCE: 77

Asp Ile Val Leu Thr Gln Ser Pro Asp Ser Leu Ala Val Ser Leu Gly
 1               5                  10                  15

Glu Arg Ala Thr Ile Asn Cys Thr Ser Ser Gln Ser Leu Leu Tyr Thr
             20                  25                  30

Ser Asn Asn Lys Asn Tyr Leu Thr Trp Tyr Gln Gln Lys Pro Gly Gln
         35                  40                  45

Pro Pro Lys Leu Leu Ile Tyr Trp Ala Ser Thr Arg Glu Phe Gly Val
     50                  55                  60

Pro Asp Arg Phe Ser Gly Ser Gly Ser Gly Thr Asp Phe Thr Leu Thr
 65                  70                  75                  80

Ile Asn Ser Leu Gln Ala Glu Asp Val Ala Thr Tyr Tyr Cys Gln Gln
                 85                  90                  95

Tyr Ser Asp Pro Pro Thr Phe Gly Gly Gly Thr Lys Leu Glu Ile
            100                 105                 110

Lys Arg Ala
        115

<210> SEQ ID NO 78
<211> LENGTH: 372
<212> TYPE: DNA
<213> ORGANISM: Homo sapiens
```

<400> SEQUENCE: 78

| | | |
|---|---|---|
| gaggtgcagg tggtggagtc tggggctgag gtgaagaagc ctggggcctc agtgaaggtt | 60 |
| tcgtgcaagg cttccggata caccttcaac agtcactata tccactgggt gcgacaggcc | 120 |
| cctggacaag gcttgagtg gatgggggg ttcatcccta tctttggcac atcaaattac | 180 |
| gcagagaagt tcaagggcag agtcaccttt accgtggaca cgtccacgaa tacagcgcac | 240 |
| atggaactga ccagactgag atctgaggac acggccatat attactgtgc actaccccgg | 300 |
| aggagcagct cgtccaagac tttctcggcc cttgactact ggggccaggg caccctggtc | 360 |
| accgtctcct ca | 372 |

<210> SEQ ID NO 79
<211> LENGTH: 387
<212> TYPE: DNA
<213> ORGANISM: Homo sapiens

<400> SEQUENCE: 79

| | | |
|---|---|---|
| caggtgcagc tgacggagtc gggggggaggc ttggtacagc cagggcggtc cctaagactc | 60 |
| tcctgtacag cctctggatt caccottggt gattatgcta tgaactgggt ccgccaggct | 120 |
| ccagggaagg gctggagtg gtaggtttc attcgaagca gaggtttcgg tgggactcca | 180 |
| gaatacgccg cgtctgtaaa aggcagattc accatctcaa gagataattc aaaggcatc | 240 |
| gcctatctgg aaatgaacag cctgaaaacc gaggacacag ccatgtatta ctgtactaga | 300 |
| gattatcgcc cattacaatt ttggcccgga cgacaaatgg atgcttttga tatttgggc | 360 |
| caagggacaa tggtcaccgt ctcttca | 387 |

<210> SEQ ID NO 80
<211> LENGTH: 357
<212> TYPE: DNA
<213> ORGANISM: Homo sapiens

<400> SEQUENCE: 80

| | | |
|---|---|---|
| caggtgcagt tggtggagtc tggagcagag gtgaaaaagg ccggggagtc tctgaagatc | 60 |
| tcctgtaagg gatctggata cagctttccc agttactgga tcaactgggt gcgccagatg | 120 |
| cccggcaaag gcctggaatg gatggggatg atctatcctg ctgactctga taccagatat | 180 |
| agcccgtcct tccaaggcca cgtcaccatc tcagccgaca gtccatcaa caccgcctac | 240 |
| ctgcaatggg ccggcctgaa ggcctcggac accgccatat attactgtgc gagacttgga | 300 |
| attggtggga ggtacatgtc tagatggggc cagggaaccc tggtcaccgt ctcctca | 357 |

<210> SEQ ID NO 81
<211> LENGTH: 357
<212> TYPE: DNA
<213> ORGANISM: Homo sapiens

<400> SEQUENCE: 81

| | | |
|---|---|---|
| caggtgcagc tggtgcagtc tggggctgag gtgaagaagc ctggggcctc agtgaaggtt | 60 |
| tcctgcgagg catctggata cactttcacc aggtactata tacactgggt gcgacaggcc | 120 |
| cctggacaag gcttgagtg gatgggaatg attaaccctc gtggtggtag cacaacctac | 180 |
| gcacagaagt tccagggcag agtcaccatg accagggaca ggtccacgag cacagtccac | 240 |
| atggaagtga gcagcctgag atctgacgac acggccgtat attactgtgc gagggagagc | 300 |
| atggttcggg acggtatgga cgtctggggc caagggacca cggtcaccgt ctcctca | 357 |

<210> SEQ ID NO 82
<211> LENGTH: 354
<212> TYPE: DNA
<213> ORGANISM: Homo sapiens

<400> SEQUENCE: 82

```
gaagtgcagt tggtggagtc tgggtctgag gtgaagaagc ctggggcctc actgaaagtc      60
tcctgcaagg cctctggata cagcttcgtc gaccactaca tccactgggt gcgacaggcc     120
cctggacaag ggcttgagtg gatgggatgg ctcaatccta atagtggtgc cacaaaatat     180
gcacagaaat tcatggcag ggtcaccctg accaggaca cgtccatcag cacagtctac     240
atggaactga gcagactgat atctgacgac acggccgtat atttctgtgc gaggggaatt     300
ttactagccc gtttggacgt ctggggccaa ggcaccctgg tcaccgtctc ctca          354
```

<210> SEQ ID NO 83
<211> LENGTH: 354
<212> TYPE: DNA
<213> ORGANISM: Homo sapiens

<400> SEQUENCE: 83

```
caggtccagc tggtgcagtc tgggggaggc ttggtccagc ctggagggtc cctgagactc      60
tcctgtgcag cctctggatt caccttcagt gattactaca tggactgggt ccgccaggct     120
ccagggaaag gctgcagtg gtggccagt ataaagcagg atggaagtga gacacgttat     180
ggggactctg tgaggggccg cttcatcata tccagagaca acaccaagaa ctcggcgtat     240
ctgcaaatga acaccctgag cgccaagac agggccgtgt atcactgtgt gagagaactt     300
gatggggat tctttgactt ctggggccag ggaaccctgg tcaccgtctc ctca          354
```

<210> SEQ ID NO 84
<211> LENGTH: 363
<212> TYPE: DNA
<213> ORGANISM: Homo sapiens

<400> SEQUENCE: 84

```
caggtgcagc tgcaggagtc gggcccagga ctggtgaagc cttcggagac cctgtccctc      60
acctgcagtg tctctggtgc ctccatgagt cgtttctact ggaattggat ccgacactcc     120
gccgggaagg gactggaatg gattggacga atctttacta tgggaccac caactacaac     180
ccctccctgg ggagtcgagt caccatgtca gttgacacgg ccaaaaacca gttctccctc     240
agagtgacct ctgtgaccgc cgcggacgcg gccgtctatt actgtgcgag aggaggcgac     300
tacggtcctg cgttggcctg gttcgacccc tggggccaag caccctggt caccgtctcc     360
tca                                                                   363
```

<210> SEQ ID NO 85
<211> LENGTH: 372
<212> TYPE: DNA
<213> ORGANISM: Homo sapiens

<400> SEQUENCE: 85

```
caggtgcagc tacaggagtg gggggaggc gtggtccagc ctggcaggtc cctgagactc      60
tcctgtgtcg cctctggatt caccttcagt ggccactgga tgcactgggt ccgccaagct     120
ccagggaagg ggctggtgtg gtctcgcgt attgatgaac atgggagcag cgcatactac     180
gcggactccg tgaacggccg attcaccatc tccagagaca acgccaagaa cacgctgtat     240
ttgcaaatga acagtctgag agccgaggat acggctgtgt attactgtgc aagattaggg     300
```

```
tttattaccc ccgaagtggt ccactggtcc tccgatatct ggggccaagg gacaatggtc    360
accgtctctt ca                                                        372
```

<210> SEQ ID NO 86
<211> LENGTH: 357
<212> TYPE: DNA
<213> ORGANISM: Homo sapiens

<400> SEQUENCE: 86

```
caggtgcagc tggtgcagtc tggggctgag gtgaagaagc ctggggcctc agtgaaggtt     60
tcctgcgagg catctggata cactttcacc aggtactata tacactgggt gcgacaggcc    120
cctggacaag gcttgagtg gatgggaatg attaaccctc gtggtggtag cacaacctac    180
gcacagaagt tccagggcag agtcaccatg accaggggaca ggtccacgag cacagtccac    240
atggaagtga gcagcctgag atctgacgac acggccgtat attactgtgc gagggagagc    300
atggttcggg acgtatggga cgtctgggc caagggacca cggtcaccgt ctcctca       357
```

<210> SEQ ID NO 87
<211> LENGTH: 375
<212> TYPE: DNA
<213> ORGANISM: Homo sapiens

<400> SEQUENCE: 87

```
ggtgcagctg gtgagtctgg ggctgaggtg aggaagcctg gtcctcggt gaaggtctcc      60 tgcaaggctt ctggaggcag catcaacaac tatgctatca gctgggtgcg acaggccct    120 ggacaagggc ttgagtggat tggagggacc ctcctcatgc tccgtattat aaactccgca    180
cagaagttcc agggcagagt ctcgattacc gcggacacat ccacgaacac ggcctacatg    240
gaactgagca gcctgagatc tgaggacacg gccatgtatt attgtgcgag cagtgtcgca    300
gcacttccaa cttctcttgg cccaatcgga tacctccacc attggggcca gggcaccctg    360
gtcaccgtct cctca                                                     375
```

<210> SEQ ID NO 88
<211> LENGTH: 351
<212> TYPE: DNA
<213> ORGANISM: Homo sapiens

<400> SEQUENCE: 88

```
ggtgcaggtg gtgagtctgg ggctgacgtg aagaagcctg gggcctcagt aaaggtctcc     60
tgcaaggctt ccggatacac cttcaccgac tactatatgc actgggtgcg acaggcccct   120
ggacaagggc ttgagtggat ggggtggatc aaccctaaca ttggtgccac aaaccatgca    180
cagaggtttc agggcaggct caccgtgagt agggacacgt ccatcaccac agtctacatg    240
gagctgagca ggctacagtc tgacgacacg gccgtctatt tttgtgcgag agatctgggg    300
atctctgctt ttgagaactg gggccaaggg acaatggtca ccgtctcttc a            351
```

<210> SEQ ID NO 89
<211> LENGTH: 360
<212> TYPE: DNA
<213> ORGANISM: Homo sapiens

<400> SEQUENCE: 89

```
ggtgacggtg gtgagtctgg ggctgaggtg aggaagcctg gggcctcagt gaaggtctcc     60
tgcaaggcct ctagatacag cttcaccgac tactttatgc actgggtgcg acaggcccct   120
ggacaagggc ttgagtggat gggatggatc aaccctaaca gtggtgtcac acactatgca    180
```

| | |
|---|---|
| cagaagtttc agggcagggt caccatgacc agggacacgt ccatcaacac agcctacatg | 240 |
| gaagtgagca ggctgagata tgacgacacg gccgtgtatt actgtacgag agaactgata | 300 |
| acaggtcgtc tgccaactga caacgactgg ggccagggaa ccctggtcac cgtctcctca | 360 |

<210> SEQ ID NO 90
<211> LENGTH: 378
<212> TYPE: DNA
<213> ORGANISM: Homo sapiens

<400> SEQUENCE: 90

| | |
|---|---|
| ggtgcagctg gtgagtctgg ggctgaggtg aggaagcctg gggcctcagt gaaggtctcc | 60 |
| tgcaagactt ccggatataa cttcaggggc tactacatac attgggtgcg acaggcccct | 120 |
| ggacaagggc ttgagtggat gggatggatc aacccgaaca ctggtggcac aaactatgca | 180 |
| cagaagtttc agggcagggt caccatgacc agggacacgt ccatcaacac agcctacatg | 240 |
| gaggtgagca agctgagatc tgacgacacg gccgtgtatt actgtgcgag acgatctgga | 300 |
| ggctcgggac gttattgggg aattaagaac aattggttcg acccctgggg ccagggcacc | 360 |
| ctggtcaccg tctcctca | 378 |

<210> SEQ ID NO 91
<211> LENGTH: 360
<212> TYPE: DNA
<213> ORGANISM: Homo sapiens

<400> SEQUENCE: 91

| | |
|---|---|
| ggtgacggtg gtgagtctgg ggctgaggtg aggaagcctg gggcctcagt gaaggtctcc | 60 |
| tgcaaggcct ctagatacag cttcaccgac tactttatgc actgggtgcg acaggcccct | 120 |
| ggacaagggc ttgagtggat gggatggatc aaccctaaca gtggtgtcac acactatgca | 180 |
| cagaagtttc agggcagggt caccatgacc agggacacgt ccatcaacac agcctacatg | 240 |
| gaagtgagca ggctgagata tgacgacacg gccgtgtatt actgtacgag agaactgata | 300 |
| gcaggtcgtc tgccaactga caacgactgg ggccagggaa ccctggtcac cgtctcctca | 360 |

<210> SEQ ID NO 92
<211> LENGTH: 366
<212> TYPE: DNA
<213> ORGANISM: Homo sapiens

<400> SEQUENCE: 92

| | |
|---|---|
| caggtccagc tggtgcagtc tggggctgag gtgaagaagc tggggcctc agtgaaggtc | 60 |
| tcctgtaagg ctgctggata caccttcacc gactactatt tcactgggt gcgacaggcc | 120 |
| cctggacaag gccttgagtg gatgggatgg atcaatcctg acagtggtgg aacaaactat | 180 |
| gcacagaagt ttcagggcag ggtcaccatg accagggaca cgtccatcag cacagcctac | 240 |
| atggacctga gcaggctgag atctgacgac acggccgtat gttactgtgc gagagggtcc | 300 |
| cgatataaca gtggctggta ttactttgac tactggagcc ggggaaccct ggtcaccgtc | 360 |
| tcctca | 366 |

<210> SEQ ID NO 93
<211> LENGTH: 360
<212> TYPE: DNA
<213> ORGANISM: Homo sapiens -continued

<400> SEQUENCE: 93

```
caggtgcagc tacaggagtg gggcccagga ctggtgaagc cttcgggac cctgtccctc    60
acctgcgctg tctctggtgg caccatcagc agtcctacct ggtggaattg ggtccgccag   120
cccccaggga aggggctgga gtggattggc gaaatctatc atagtggaac ctcccaccac   180
aacccgtccc tcaagaatcg agtcacctta tcagtagaca gtccaagaa ccagttctcc   240
ctgaagctga actctatgac cgccgcggac acggccgtgt atttctgtac gagactggat   300
ttcgattccc cactcggtat ggacgcctgg ggccaaggga ccacggtcac cgtctcctca   360
```

<210> SEQ ID NO 94
<211> LENGTH: 327
<212> TYPE: DNA
<213> ORGANISM: Homo sapiens

<400> SEQUENCE: 94

```
gacatcgtga tgacccggtc tccatcctcc ctgtctgcat ctgtaggaga cagagtcacc    60
atcacttgcc gggcaagtca gagcattagc acctatttaa attggtatca gcagaaagca   120
gggaaagccc ctaaactcct gatctatgct gcatccagtt tgcaaagtgg ggtcccctca   180
aggttcagtg gcagtggatc tgggacagat ttcactctca ccatcagcag tctgcaacct   240
gaagattttg caacttacta ctgtcaacag agttacagta cccctcgaac gttcggccaa   300
gggaccaagg tggaaatcaa acgtgcg                                       327
```

<210> SEQ ID NO 95
<211> LENGTH: 330
<212> TYPE: DNA
<213> ORGANISM: Homo sapiens

<400> SEQUENCE: 95

```
gaaattgtgt tgacgcagtc tccatcttct gtgtctgcat ctgtgggaga cagagtcacc    60
atcacttgtc gggcgagtga ggatgttaac agctggttag cctggtatca gcagaagcca   120
gggaaagccc ctaagctcct gatctatggt tcaaccaatt tgcaaggtgg ggtcccatca   180
aggttcagcg gacgtggatc tgggacacac tttactttca ccatcaacgg cctgcagcct   240
gaagatattg caacatatta ctgtaaatat tttgatgctc ccctccggt caccttcggc   300
caagggacac gactggagat taaacgtgcg                                    330
```

<210> SEQ ID NO 96
<211> LENGTH: 345
<212> TYPE: DNA
<213> ORGANISM: Homo sapiens

<400> SEQUENCE: 96

```
gacatcgtgc tgacccagtc tccagactcc ctggctgtgt ctctgggcga gagggccacc    60
atcaactgca cgtccagcca gagtctttta tacacctcca acaataagaa ctacttaact   120
tggtaccaac agaaaccagg gcagcctcct aaactcctca tttactgggc atctacccgg   180
gaattcggcg tccctgaccg attcagtggc agcgggtctg ggacagattt cactctcacc   240
atcaacagcc tgcaggctga agatgtggcg acttattact gtcagcaata ttctgatcct   300
cctcccactt tcggcggagg gaccaagctg gagatcaaac gtgcg                   345
```

<210> SEQ ID NO 97
<211> LENGTH: 708
<212> TYPE: DNA
<213> ORGANISM: Homo sapiens -continued

```
<400> SEQUENCE: 97
gatatcgtcc tgacccagag cccggcgacc ctctcggtca cccccggcaa ctcggtgtcc    60
ctctcgtgcc gcgcctcgca gtcgatcggc aacaacctcc actggtatca gcagaagtcg   120
cacgagagcc cgcgcctcct gatcaagtac gccagccagt cgatctcggg gatcccgtcg   180
cgcttcagcg gctcgggctc gggcaccgac ttcaccctgt cgatcaacag cgtcgagacg   240
gaggacttcg gcatgtactt ctgccagcag tcgaacagct ggccgtacac cttcggcggc   300
ggtaccaagc tgatcatcac ggccggcggg ggcggtagcg gcggtggcgg gtcgggcggt   360
ggcggatcgg atatccagct gcaggagtcg ggcccgagcc tcgtcaagcc gtcgcagacc   420
ctgtcgctca cctgcagcgt caccggcgac tcgatcacct cggactactg gtcgtggatc   480
cgcaagttcc ccggcaaccg cctcgagtac atgggctacg tcagctactc gggcagcacc   540
tactacaacc cctcgctgaa gagccgcatc tcgatcaccc gcgacacctc caagaaccag   600
tactacctgg acctcaactc ggtcaccacc gaggacaccg ccacctacta ctgcgcgaac   660
tgggacggcg actactgggg ccagggcacc ctcgtcaccg tctccgcg                708

<210> SEQ ID NO 98
<211> LENGTH: 236
<212> TYPE: PRT
<213> ORGANISM: Artificial
<220> FEATURE:
<223> OTHER INFORMATION: HEL binding single chain-Fv coding DNA

<400> SEQUENCE: 98

Asp Ile Val Leu Thr Gln Ser Pro Ala Thr Leu Ser Val Thr Pro Gly
 1               5                  10                  15

Asn Ser Val Ser Leu Ser Cys Arg Ala Ser Gln Ser Ile Gly Asn Asn
             20                  25                  30

Leu His Trp Tyr Gln Gln Lys Ser His Glu Ser Pro Arg Leu Leu Ile
         35                  40                  45

Lys Tyr Ala Ser Gln Ser Ile Ser Gly Ile Pro Ser Arg Phe Ser Gly
     50                  55                  60

Ser Gly Ser Gly Thr Asp Phe Thr Leu Ser Ile Asn Ser Val Glu Thr
 65                  70                  75                  80

Glu Asp Phe Gly Met Tyr Phe Cys Gln Gln Ser Asn Ser Trp Pro Tyr
                 85                  90                  95

Thr Phe Gly Gly Gly Thr Lys Leu Ile Ile Thr Ala Gly Gly Gly Gly
            100                 105                 110

Ser Gly Gly Gly Gly Ser Gly Gly Gly Ser Asp Ile Gln Leu Gln
        115                 120                 125

Glu Ser Gly Pro Ser Leu Val Lys Pro Ser Gln Thr Leu Ser Leu Thr
    130                 135                 140

Cys Ser Val Thr Gly Asp Ser Ile Thr Ser Asp Tyr Trp Ser Trp Ile
145                 150                 155                 160

Arg Lys Phe Pro Gly Asn Arg Leu Glu Tyr Met Gly Tyr Val Ser Tyr
                165                 170                 175

Ser Gly Ser Thr Tyr Tyr Asn Pro Ser Leu Lys Ser Arg Ile Ser Ile
            180                 185                 190

Thr Arg Asp Thr Ser Lys Asn Gln Tyr Tyr Leu Asp Leu Asn Ser Val
        195                 200                 205
```

Thr Thr Glu Asp Thr Ala Thr Tyr Tyr Cys Ala Asn Trp Asp Gly Asp
    210                 215                 220

Tyr Trp Gly Gln Gly Thr Leu Val Thr Val Ser Ala
225                 230                 235

<210> SEQ ID NO 99
<211> LENGTH: 36
<212> TYPE: DNA
<213> ORGANISM: Artificial
<220> FEATURE:
<223> OTHER INFORMATION: SBA-15-binding peptide coding DNA

<400> SEQUENCE: 99
atccccatgc acgtgcacca caagcacccc cacgtg                                  36

<210> SEQ ID NO 100
<211> LENGTH: 12
<212> TYPE: PRT
<213> ORGANISM: Artificial
<220> FEATURE:
<223> OTHER INFORMATION: SBA-15-binding peptide

<400> SEQUENCE: 100

Ile Pro Met His Val His His Lys His Pro His Val
1               5                   10

<210> SEQ ID NO 101
<211> LENGTH: 426
<212> TYPE: DNA
<213> ORGANISM: Artificial
<220> FEATURE:
<223> OTHER INFORMATION: SBA-binding peptide fused pVIII coding DNA

<400> SEQUENCE: 101
ggatcctcta gagtcggctt tacactttat gcttccggct cgtataatgt gtggaattgt         60
gagcgctcac aattgagctc aggaggctta ctatgaagaa atctctggtt cttaaggcta        120
gcgttgctgt cgcgaccctg gtacctatgt tgtccttcgc tatccccatg cacgtgcacc        180
acaagcaccc ccacgtggct gaaggtgatg atccggccaa ggcggccttc aattctctgc        240
aagcttctgc taccgagtat attggttacg cgtgggccat ggtggtggtt atcgttggtg        300
ctaccatcgg gatcaaactg ttcaagaagt ttacttcgaa ggcgtcttaa tgatagggtt        360
accagtctaa gcccgcctaa tgagcgggct ttttttttat cgagacctgc aggtcgaccg        420
gcatgc                                                                  426

<210> SEQ ID NO 102
<211> LENGTH: 747
<212> TYPE: DNA
<213> ORGANISM: Artificial
<220> FEATURE:
<223> OTHER INFORMATION: SBA-binding peptide fused pVIII

<400> SEQUENCE: 102
ggatcctcta gagtcggctt tacactttat gcttccggct cgtataatgt gtggaattgt         60
gagcgctcac aattgagctc aggaggctta ctatgaagaa atctctggtt cttaaggcta        120
gcgttgctgt cgcgaccctg gtacctatgt tgtccttcgc tcaggtgcag ttggtggagt        180
ctggagcaga ggtgaaaaag gccggggagt ctctgaagat ctcctgtaag ggatctggat        240
acagctttcc cagttactgg atcaactggg tgcgccagat gcccggcaaa ggcctggaat        300

```
ggatggggat gatctatcct gctgactctg ataccagata tagcccgtcc ttccaaggcc    360
acgtcaccat ctcagccgac aagtccatca acaccgccta cctgcaatgg gccggcctga    420
aggcctcgga caccgccata tattactgtg cgagacttgg aattggtggg aggtacatgt    480
ctagatgggg ccagggaacc ctggtcaccg tctcctcagc tgaaggtgat gatccggcca    540
aggcggcctt caattctctg caagcttctg ctaccgagta tattggttac gcgtgggcca    600
tggtggtggt tatcgttggt gctaccatcg ggatcaaact gttcaagaag tttacttcga    660
aggcgtctta atgatagggt taccagtcta agcccgccta atgagcgggc ttttttttta    720
tcgagacctg caggtcgacc ggcatgc                                        747

<210> SEQ ID NO 103
<211> LENGTH: 35
<212> TYPE: DNA
<213> ORGANISM: Artificial
<220> FEATURE:
<223> OTHER INFORMATION: 7s4_fw_NcoI

<400> SEQUENCE: 103
acatgccatg gcccaggtgc agttggtgga gtctg                               35

<210> SEQ ID NO 104
<211> LENGTH: 34
<212> TYPE: DNA
<213> ORGANISM: Artificial
<220> FEATURE:
<223> OTHER INFORMATION: HEL-bk-Hind3

<400> SEQUENCE: 104
aatggcaagc ttggccgtga tgatcagctt ggta                                34

<210> SEQ ID NO 105
<211> LENGTH: 43
<212> TYPE: DNA
<213> ORGANISM: Artificial
<220> FEATURE:
<223> OTHER INFORMATION: Lac delta alpha_fw

<400> SEQUENCE: 105
cccggatccg cggccgccat gaccatgtta cggaattcac tgg                      43

<210> SEQ ID NO 106
<211> LENGTH: 36
<212> TYPE: DNA
<213> ORGANISM: Artificial
<220> FEATURE:
<223> OTHER INFORMATION: Lac delta alpha_bk

<400> SEQUENCE: 106
cccccctcga gttattttg acaccagacc aactgg                               36

<210> SEQ ID NO 107
<211> LENGTH: 43
<212> TYPE: DNA
<213> ORGANISM: Artificial
<220> FEATURE:
<223> OTHER INFORMATION: Lac delta omega_fw

<400> SEQUENCE: 107
cccggatccg cggccgccat gaccatgatt acggattcac tgg                      43
```

```
<210> SEQ ID NO 108
<211> LENGTH: 32
<212> TYPE: DNA
<213> ORGANISM: Artificial
<220> FEATURE:
<223> OTHER INFORMATION: Lac delta omega_bk

<400> SEQUENCE: 108
cccccctcga gttacggtgc acgggtgaac tg                                32

<210> SEQ ID NO 109
<211> LENGTH: 30
<212> TYPE: DNA
<213> ORGANISM: Artificial
<220> FEATURE:
<223> OTHER INFORMATION: scFv(HEL)_fw

<400> SEQUENCE: 109
acatgccatg ggatatcgtc ctgacccaga                                   30

<210> SEQ ID NO 110
<211> LENGTH: 33
<212> TYPE: DNA
<213> ORGANISM: Artificial
<220> FEATURE:
<223> OTHER INFORMATION: scFv(HEL)_bk

<400> SEQUENCE: 110
aatggcaagc ttcgcggaga cggtgacgag ggt                               33

<210> SEQ ID NO 111
<211> LENGTH: 33
<212> TYPE: DNA
<213> ORGANISM: Artificial
<220> FEATURE:
<223> OTHER INFORMATION: 7s4_fw_NcoI_2

<400> SEQUENCE: 111
acatgccatg gcaggtgcag ttggtggagt ctg                               33

<210> SEQ ID NO 112
<211> LENGTH: 30
<212> TYPE: DNA
<213> ORGANISM: Artificial
<220> FEATURE:
<223> OTHER INFORMATION: primer for scFv-f
<220> FEATURE:
<221> NAME/KEY: misc_feature
<222> LOCATION: (1)..(4)
<223> OTHER INFORMATION: n is a, c, g, or t

<400> SEQUENCE: 112
nnnnccatgc ccgatatcgt cctgacccag                                   30

<210> SEQ ID NO 113
<211> LENGTH: 27
<212> TYPE: DNA
<213> ORGANISM: Artificial
<220> FEATURE:
<223> OTHER INFORMATION: primer for scFv-r

<400> SEQUENCE: 113
agctaccgcg gagacggtga cgagggt                                      27
```